(12) United States Patent  (10) Patent No.: US 9,259,174 B2
Schraga  (45) Date of Patent: Feb. 16, 2016

(54) RETRACTABLE FLUID COLLECTION DEVICE

(75) Inventor: Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 2242 days.

(21) Appl. No.: 11/738,240

(22) Filed: Apr. 20, 2007

(65) Prior Publication Data

US 2008/0262421 A1  Oct. 23, 2008

(51) Int. Cl.
*A61B 5/00* (2006.01)
*A61B 5/15* (2006.01)

(52) U.S. Cl.
CPC .................................. *A61B 5/1444* (2013.01)

(58) Field of Classification Search
USPC ......... 604/181, 187, 110, 229, 264, 272, 403, 604/164.01, 164.12, 180, 192, 194, 195, 604/198, 200, 263, 274; 600/576–578, 583
See application file for complete search history.

(56) References Cited

U.S. PATENT DOCUMENTS

| | | | |
|---|---|---|---|
| 4,813,426 A | 3/1989 | Haber et al. | |
| 4,838,863 A | 6/1989 | Allard et al. | |
| 4,915,702 A * | 4/1990 | Haber | 604/198 |
| 4,994,034 A * | 2/1991 | Botich et al. | 604/110 |
| 5,114,410 A * | 5/1992 | Caralt Batlle | 604/195 |
| 5,180,370 A * | 1/1993 | Gillespie | 604/110 |
| 5,385,551 A * | 1/1995 | Shaw | 604/110 |
| 5,407,436 A * | 4/1995 | Toft et al. | 604/195 |
| 5,423,758 A | 6/1995 | Shaw | |
| 5,578,011 A * | 11/1996 | Shaw | 604/110 |
| 5,632,733 A * | 5/1997 | Shaw | 604/195 |
| 5,810,775 A * | 9/1998 | Shaw | 604/110 |
| 6,015,438 A * | 1/2000 | Shaw | 604/195 |
| 6,024,710 A | 2/2000 | Miller | |
| 6,171,284 B1 * | 1/2001 | Kao et al. | 604/192 |
| 6,432,087 B1 * | 8/2002 | Hoeck et al. | 604/181 |
| 6,572,565 B2 | 6/2003 | Daley et al. | |
| 6,932,793 B1 * | 8/2005 | Marshall et al. | 604/135 |
| 7,521,022 B2 * | 4/2009 | Konrad | 422/103 |
| 7,553,293 B2 * | 6/2009 | Jensen et al. | 604/110 |

* cited by examiner

*Primary Examiner* — Scott Medway
(74) *Attorney, Agent, or Firm* — Greenblum & Bernstein, P.L.C.

(57) ABSTRACT

Retractable medical device including a body having an open back end and a front end. A movable member is arranged within the body. The movable member has a back end and a front end. A needle holding member is arranged in an area of the front end of the movable member. A spring is structured and arranged to move the needle holding member to a retracted position within the movable member when the movable member experiences at least one of: the front end of the movable member is caused to expand generally radially; the back end of the movable member is caused to contract generally radially; the front end of the movable member is caused to expand generally radially when the back end of the movable member is caused to contract generally radially; and axial movement caused by a cap closing off the back end of the body which engages a tapered surface of the back end of the movable member. This Abstract is not intended to define the invention disclosed in the specification, nor intended to limit the scope of the invention in any way.

44 Claims, 36 Drawing Sheets

Fig. 4 — PRIOR ART

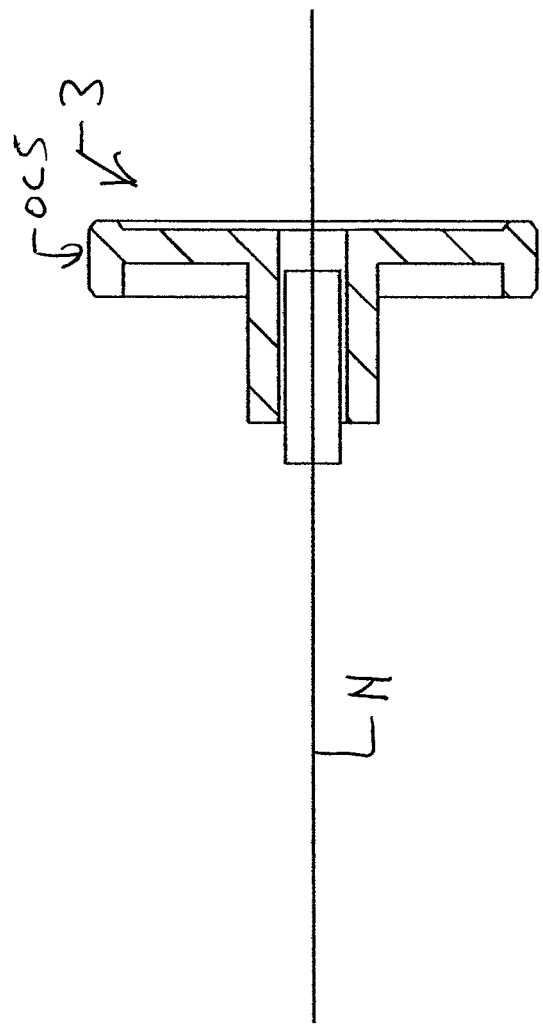
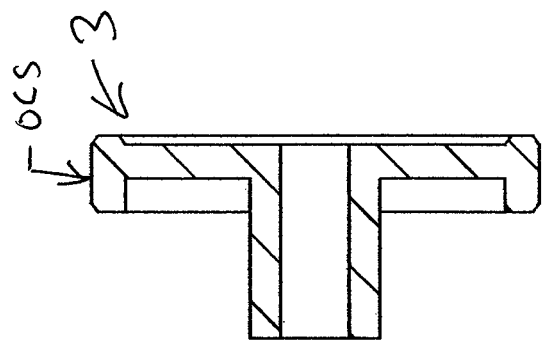

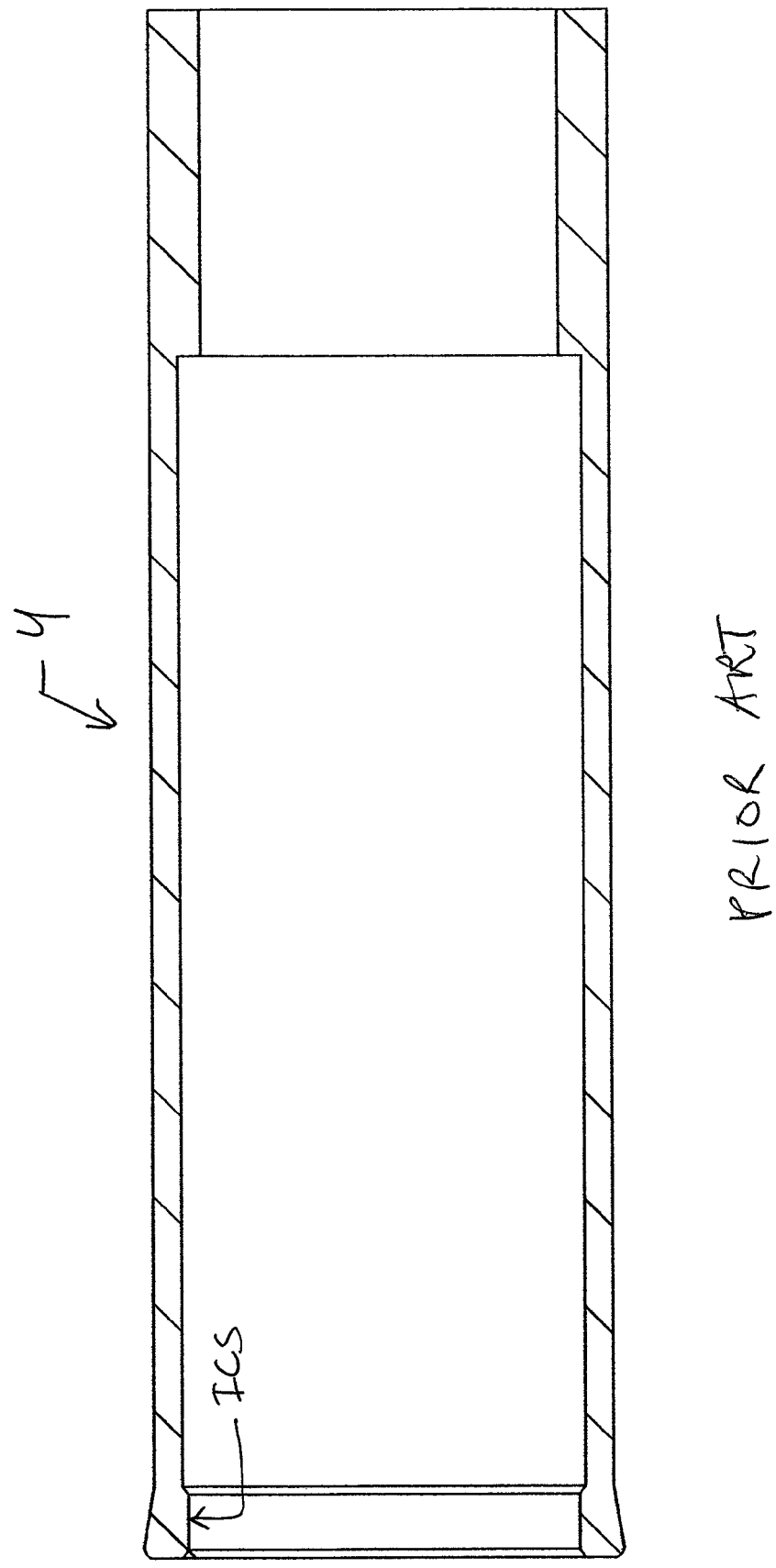

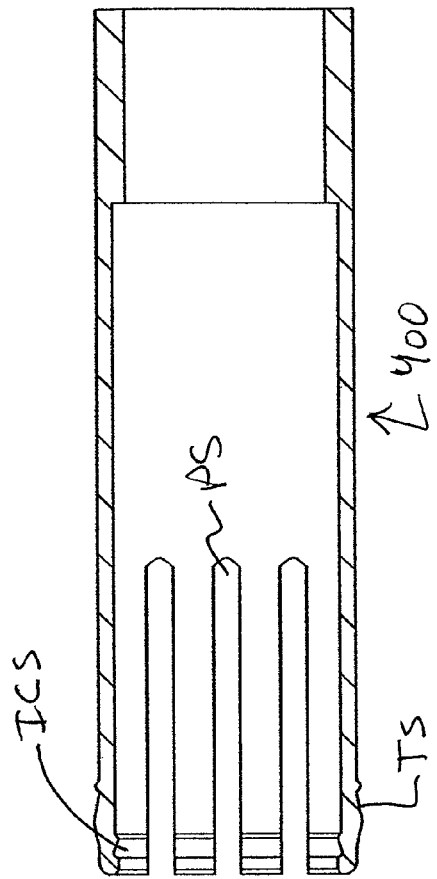

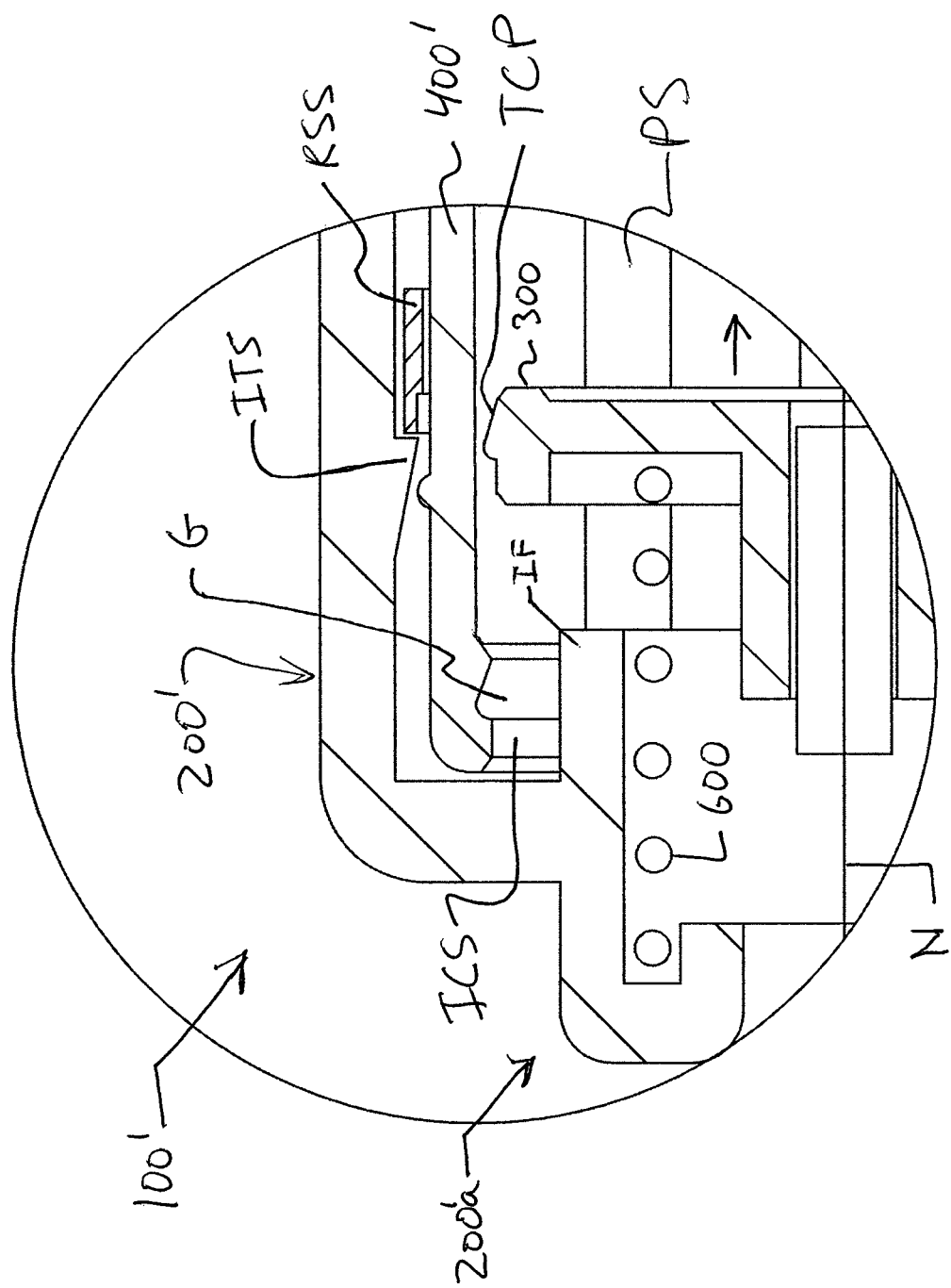

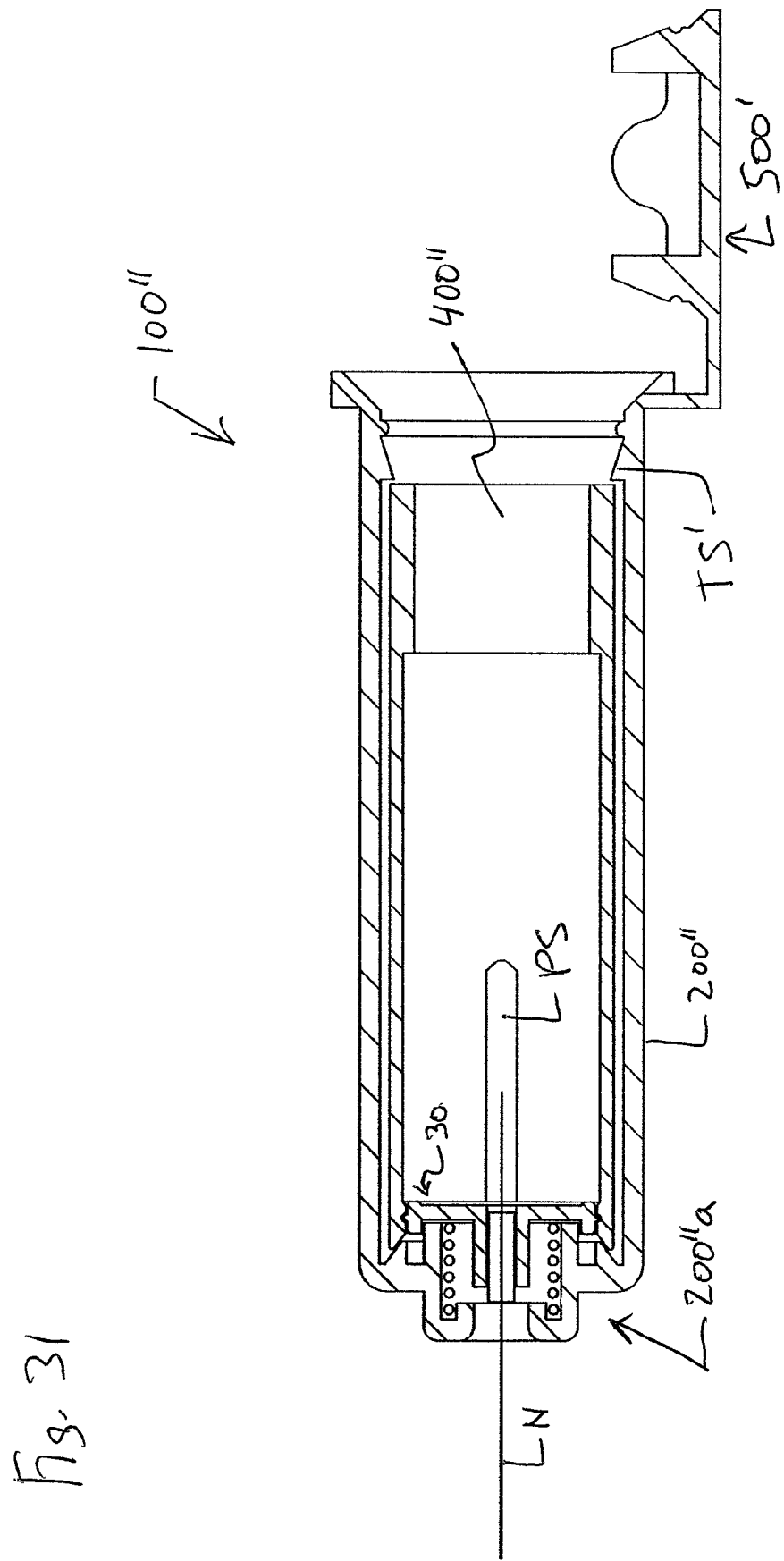

RETRACTABLE FLUID COLLECTION DEVICE

BACKGROUND OF THE INVENTION

1. Field of the Invention

This invention relates generally to devices used to collect fluid samples from patients. More specifically, this invention relates to a device which utilizes a holder having a double-ended needle that can be retracted into the holder when a cap of the holder is closed. The invention also relates to a method of collecting a fluid sample with the device as well as a method of making the device. The invention also relates to a blood sample collection device that automatically retracts the double-ended needle into the holder after a cap closes off the open end of the holder 2. Discussion of Background Information Prevention of needle sticks is of paramount concern in the healthcare industry because of serious and deadly risk factors associated with AIDS and other serious communicable diseases. Typical blood collection devices utilize a needle inserted into a patient's vein so as to draw blood through the needle into an associated separate collection reservoir. Accidental needle sticks from previously used needles can occur during the fluid withdrawing process and subsequent handling and disposal operation. Until such used medical devices are destroyed, they remain a risk to those handling them.

Devices used for blood sampling are well know and include a collection device sold under the trademark Vacutainer® by Becton Dickinson Corporation. This device has a tubular syringe-like body with a needle in the front end, part of which extends back into a tubular syringe-like shell. Part of the needle extends externally for punching the skin. An evacuated collection tube with a rubber stopper is placed into the open back of the syringe-like shell with the rubber stopper against the internal end of the needle. After the skin is punctured, the collection tube is pushed forward to cause the needle to enter the evacuated tube. Vacuum helps draw blood into the collecting tube. When a sufficient sample has been obtained, the collecting tube and the stopper are simply withdrawn from the tubular shell and sent to the laboratory. This particular device has a permanently extended needle and an opening in the back for the collection tube which remains open after the collection tube is removed, leaving small quantities of blood and an internally exposed needle.

Retractable medical devices which are used for collecting fluid samples from patients are also known. An early example of such a device is U.S. Pat. No. 4,813,426 which employs a mechanically translatable insert holding a double-ended needle. This device has a position which compresses a spring portion of the holder. When buttons extending from opposite sides of the outer tube are compressed, the needle carrier can be mechanically moved to the position of us or to a rearward safe position. U.S. Pat. No. 4,838,863 describes a spring loaded double ended needle carrier in a T-shaped housing having an opening behind for the sample tube. The needle holder is locked in a use position with a removable pin which is withdrawn to retract the needle. Alternately, breakable tabs on the needle holder extend laterally under a shelf with pins which may be pushed down when the sample tube is inserted to fracture the breakable tabs thereby releasing the needle holder which is withdrawn into the interior as the sample tube is removed. Subsequently, a cap is provided to close the back. Allard does not explain how one could assemble the device without making the outer body in two or more pieces.

Other devices attach the double ended needle to a partially withdrawable plunger with an opening in back for the sample tube. U.S. Pat. No. 5,423,758 to shaw, the disclosure of which is hereby expressly incorporated by reference in its entirety, utilizes a tubular outer body with a partially movable plunger. The plunger has a separable needle holding portion for a double ended needle and an opening in the back of the plunger for a sample tube. It utilizes a two position end cap from which the sample tube extends. The plunger is used to position and retract the needle assembly. U.S. Pat. No. Re 39,107 to shaw, the disclosure of which is hereby expressly incorporated by reference in its entirety, similarly utilizes a tubular outer body with a partially movable plunger. The plunger has a separable needle holding portion for a double ended needle and an opening in the back of the plunger for a sample tube. It utilizes a two position end cap from which the sample tube extends. The plunger is used to position and retract the needle assembly.

The invention aims to improper devices of the type disclosed in U.S. Pat. Nos. 5,423,758 and Re 39,107 to shaw by providing a releasable locking connection between the plunger and the needle holding portion and/or by causing the connection between these two members to release when the plunger experiences pivoting movement.

A conventional blood collection device of the type described above is shown in FIGS. 1-10 wherein the device 1 has an outer sleeve member 2 which includes a proximal end 2a which is configured to allow an external needle N of a double-ended needle member or holder 3 to pass therethrough and a distal end 2b which can be closed off by a cap 5. The needle holder 3 has an outer circumferential surface OCS which frictionally engages with an inner circumferential surface ICS of a proximal end of an inner sleeve 4. The device 1 also includes a spring 6 which functions to move the needle holder 3 when the outer circumferential surface OCS of the needle holder 3 no longer frictionally engages with the inner circumferential surface ICS of the proximal end of the inner sleeve 4. As is shown from FIG. 4, it is believed that the device 1 functions as follows: once a user moves the cap 5 to the closed position, the sleeve 4 is caused to move axially in the proximal direction, which, in turn, causes the outer circumferential surface OCS of the needle holder 3 to disengage from the inner circumferential surface ICS of the proximal end of the inner sleeve 4. The spring 6 is then free to move the needle holder 3 within the sleeve 4 in a distal direction which ensures that the needle holder 3 is fully and safely arranged within the device 1. The device 1 can then be safely handled and discarded.

SUMMARY OF THE INVENTION

According to one non-limiting aspect of the invention there is provided a retractable medical device comprising a body having an open back end and a front end, a movable member arranged within the body, the movable member having a back end and a front end, a needle holding member arranged in an area of the front end of the movable member, and a spring structured and arranged to move the needle holding member to a retracted position within the movable member when the movable member experiences at least one of: the front end of the movable member is caused to expand generally radially; the back end of the movable member is caused to contract generally radially; the front end of the movable member is caused to expand generally radially when the back end of the movable member is caused to contract generally radially; and axial movement caused by a cap closing off the back end of the body which engages a tapered surface of the back end of the movable member.

The body and the movable members can be at least one of generally cylindrical and generally tubular. The movable member may be sized and configured to at least partially receive therein one of a fluid collection tube and an evacuated blood collection receptacle. An outer peripheral surface of the needle holding member may frictionally engage with an inner surface of the front end of the movable member. An outer peripheral surface of the needle holding member may comprise at least one projection which engages with at least one recess arranged on an inner surface of the front end of the movable member. An outer peripheral surface of the needle holding member may comprise at least one recess which engages with at least one projection arranged on an inner surface of the front end of the movable member. The body may comprise a device arranged within the body for limiting axial movement of the movable member within the body.

The device may further comprise a cap structure and arranged to close off a back end of the body. The device may further comprise a cap connected by a living hinge to the body. The device may further comprise a cap having a portion which contacts the back end of the movable member. The device may further comprise a cap having tapered surfaces which contact tapered surfaces of the back end of the movable member. The device may further comprise a cap structured and arranged to lock to the back end of the body. The device may further comprise a cap structured and arranged to cause the needle holding member to move to the retracted position by the spring when the cap is locked to the body. The device may further comprise a cap structured and arranged to cause the needle holding member to move to the retracted position by the spring when the cap closes off the back end of the body. The device may further comprise a cap structured and arranged to cause the needle holding member to move to the retracted position by the spring when the cap engages with a back end of the movable member.

The movable member may comprise an internal surface which limits retraction movement of the needle holding member. The movable member may comprise an internal annular surface which limits retraction movement of the needle holding member. The needle holder may be structured and arranged to support a double-ended needle. The needle holder may be structured and arranged to retain a removable double-ended needle.

The device may further comprise a cap having an outer rim larger than an opening in the back of the body and an inner rim comprising at least one protrusion structured and arranged to engage with the back end of the movable member. The device may further comprise a cap having an outer rim larger than an opening in the back of the body and at least two oppositely arranged protrusions structured and arranged to engage with the back end of the movable member. The device may further comprise a cap having an outer rim larger than an opening in the back of the body and at least two oppositely arranged tapered protrusions structured and arranged to engage with tapered surfaces of the back end of the movable member.

The movable member may comprise oppositely arranged elongated slots extending to the front end of the movable member, whereby a width of the elongated slots changes when the needle holding member is caused to move to the retracted position. The movable member may comprise oppositely arranged elongated slots extending to the back end of the movable member, whereby a width of the elongated slots changes when the needle holding member is caused to move to the retracted position. The movable member may comprise oppositely arranged first elongated slots extending to the front end of the movable member and oppositely arranged second elongated slots extending to the back end of the movable member, whereby a width of the elongated first and second slots changes when the needle holding member is caused to move to the retracted position. The movable member may comprise first elongated slots extending to the front end of the movable member and second elongated slots extending to the back end of the movable member, whereby a width of the elongated first and second slots changes when the needle holding member is caused to move to the retracted position. The movable member comprises first elongated slots extending to the front end of the movable member, second elongated slots extending to the back end of the movable member, and a connecting portion disposed between the first and second elongated slots, whereby a width of the elongated first and second slots changes when the needle holding member is caused to move to the retracted position. The movable member may comprise two-semi-cylindrical members which, when arranged to form a cylindrical member, form first elongated slots extending to the front end of the movable member, second elongated slots extending to the back end of the movable member, and a connecting portion disposed between the first and second elongated slots, whereby a width of the elongated first and second slots changes when the needle holding member is caused to move to the retracted position. The movable member may comprise at least one elongated slot extending to the front end of the movable member and a tapered surface arranged at the front end of the movable member which is structured and arranged to engage a tapered surface inside the body to thereby cause the needle holding member to move to the retracted position. The movable member may comprise at least two oppositely arranged slots extending to the front end of the movable member and a tapered surface arranged at the front end of the movable member which is structured and arranged to engage a tapered surface inside the body to thereby cause the needle holding member to move to the retracted position. The movable member may comprise at least one slot extending to the front end of the movable member and the body comprises at least one projection having tapered surfaces which are structured and arranged to engage the at least one slot to thereby cause the needle holding member to move to the retracted position. The movable member may comprise at least one slot arranged on the front end of the movable member and the body comprises at least one projection having tapered surfaces, and wherein the slot engages with the tapered surfaces, a width of the at least one slot changes to thereby cause the needle holding member to move to the retracted position. The movable member may comprise at least two oppositely arranged slots arranged on the front end of the movable member and the body comprises at least two oppositely arranged projections each having tapered surfaces, and wherein each slot engages with each set of the tapered surfaces, a width of each slot changes to thereby cause radial expansion of the front end of the movable member. The movable member may comprise at least one slot extending to the front end of the movable member and the body comprises at least one projection arranged in an inner cylindrical surface of the body between the front end and the back end of the body, and wherein the at least one slot comprises tapered surfaces structured and arranged to engage with the at least one projection, whereby a width of the at least one slot changes when the movable member moves axially within the body and when the tapered surfaces engage with the at least one projection. The body may comprise at least one projection arranged in an inner cylindrical surface of the body between the front end and the back end of the body and wherein the at least one projection is structured and arranged to serve as an axle which allows portions of the movable member to pivot about the axle. The body may comprise oppositely arranged projections arranged in an inner cylindrical surface of the body between the front end and the back end of the body and wherein each projection is structured and arranged to serve as an axle which allows portions of the movable member to pivot about the axle.

The invention also provides for a retractable medical device comprising a tubular body having an open back end and a front end, a movable sleeve arranged within the body, the movable sleeve having a back end and a front end, the movable sleeve being sized and configured to at least partially receive therein one of a fluid collection tube and an evacuated blood collection receptacle, a needle holding member comprising a centrally disposed opening for receiving a double-ended needle and being axially retained in an area of the front end of the movable sleeve, a spring structured and arranged to move the needle holding member to a retracted position within the movable sleeve, and a cap structured and arranged to close-off the back end of the tubular body, wherein, when the cap is positioned to close-off the back end of the tubular body, at least one of: the movable sleeve experiences axial movement which participates in causing the front end of the movable sleeve to expand generally radially; the back end of the movable sleeve experiences radial contraction which causes the front end of the movable sleeve to expand generally radially; and the back end of the movable sleeve experiences radial contraction which causes portions of the front end of the movable sleeve to pivot open.

The invention also provides for a single-use blood sampling device comprising a tubular body having an open back end and a front end, a sleeve arranged within the body, the sleeve having a back end and a front end, the sleeve being sized and configured to at least partially receive therein one of a fluid collection tube and an evacuated blood collection receptacle, a needle holding member comprising a centrally disposed opening for receiving a double-ended needle and being axially retained in an area of the front end of the sleeve, a spring structured and arranged to move the needle holding member to a retracted position within the sleeve, and a cap structured and arranged to close-off the back end of the tubular body, wherein, when the cap is positioned to close-off the back end of the body, the needle holding member is automatically caused to move to the retracted position within the sleeve as a result of at least one of: the sleeve experiencing axial movement which participates in causing the front end of the sleeve to expand generally radially; the back end of the sleeve experiencing radial contraction which causes the front end of the sleeve to expand generally radially; and the back end of the sleeve experiencing radial contraction which causes portions of the front end of the sleeve to pivot open.

The invention also provides for a method of taking a fluid sample using the device of the type described above, wherein the method comprises inserting a receptacle into the device, removing the receptacle from the device, and placing a cap onto the back end of the body to thereby cause the needle holding member to move to the retracted position.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 7 shows a cross-section view of the needle holding member used in the embodiment shown in FIG. 1;

FIG. 8 shows a cross-section view of the needle holding member and a conventional type double-ended needle mounted thereto and used in the embodiment shown in FIG. 1;

FIG. 9 shows a cross-section view of the movable member used in the embodiment shown in FIG. 1;

FIG. 22 also shows what happens after the cap is moved to the closed position, i.e., the front of the movable member is cause to expand generally radially (thereby releasing its engagement with the needle holding member) by a radially contracting the rear end of the movable member with the aid of the cap;

FIG. 27 shows a side cross-section view of the needle holding member with a conventional type double-ended needle mounted thereto and which is used in the embodiment shown in FIG. 25;

FIG. 28 shows a side cross-section view of the movable member which is used in the embodiment shown in FIG. 25;

FIG. 29 shows a side cross-section view of the ring which is used in the embodiment shown in FIG. 25;

FIG. 30 shows an enlarged cross-section view of a portion of FIG. 25 and after the ring is caused to move distally and after the movable member is caused to release from engagement with the needle holding member;

FIG. 31 shows a cross-section view of still another embodiment of the blood collection device. The device utilizes an annular outwardly tapered projection on an inside surface of the outer body which engages with an inwardly tapered leading end of the movable member to cause the front or proximal end of the movable member to expand radially when the movable member moves relative to the needle holding member. This would occur when the cap is moved to the closed position;

DETAILED DESCRIPTION OF THE INVENTION

Figure 1:
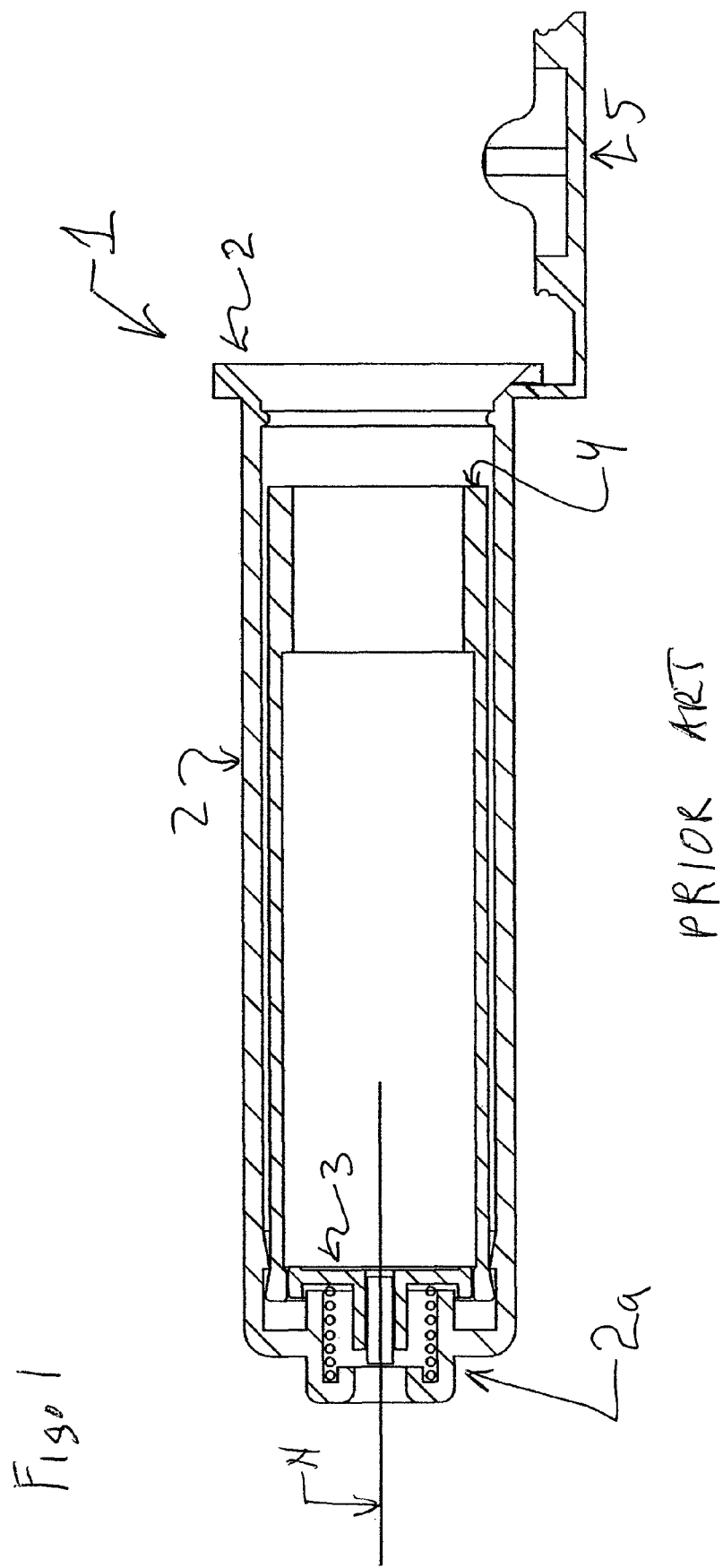
FIG. 1 shows a cross-section view of a type of prior art blood collection device. The device is shown in a prior-use or packaged position and is ready to receive therein a collection tube.
Figure 2:
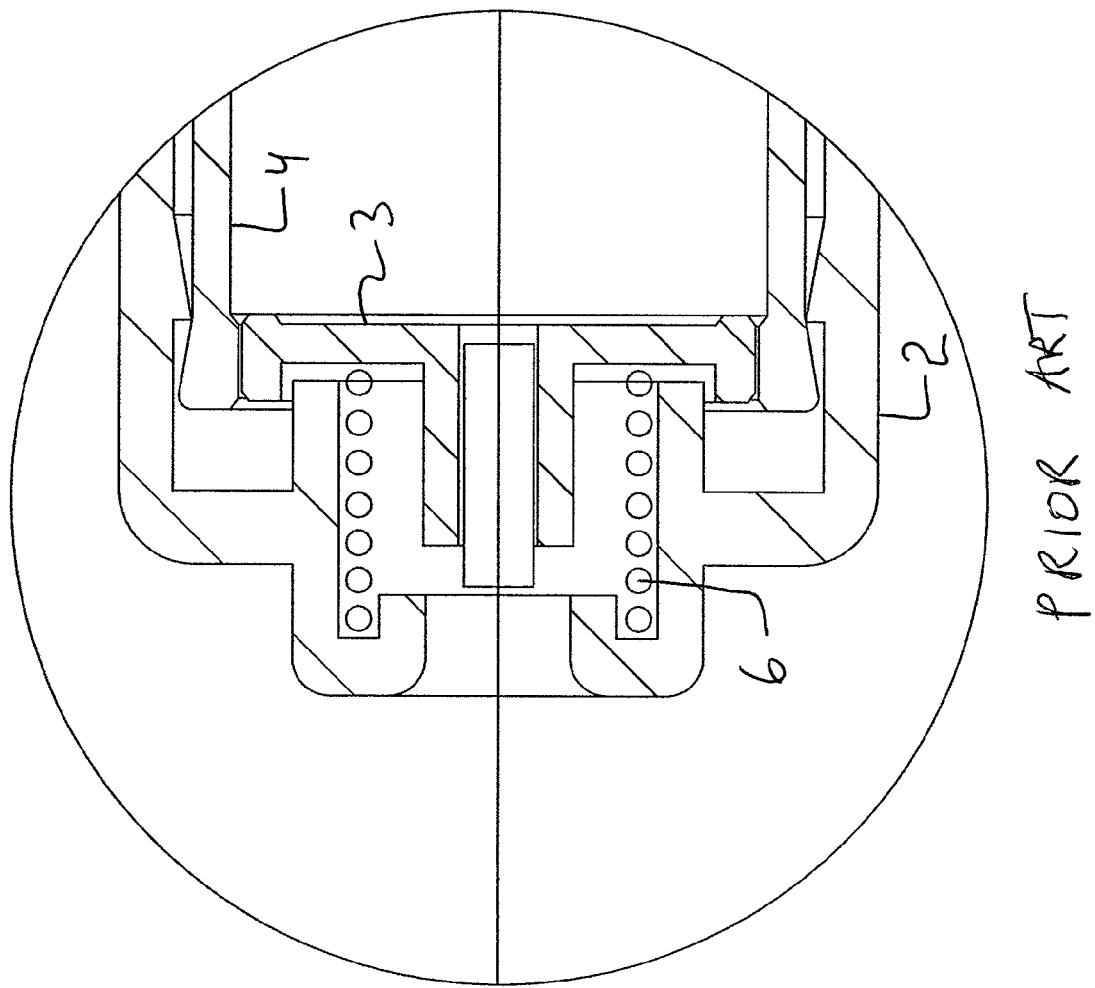
FIG. 2 shows an enlarged cross-section view of a portion of FIG. 1.
Figure 3:
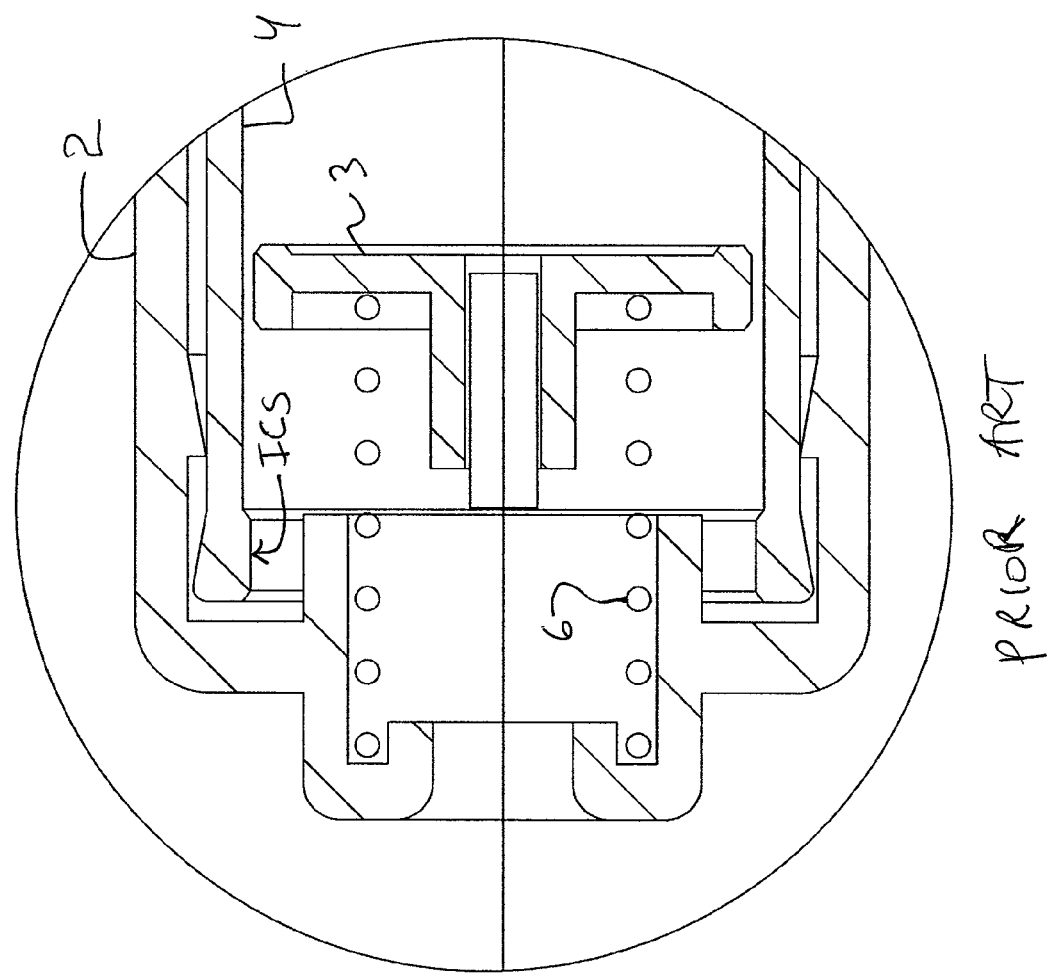
FIG. 3 shows an enlarged cross-section view of FIG. 2 after the cap is moved to the closed position thereby causing the needle holding member to move towards the retracted position.
Figure 4:
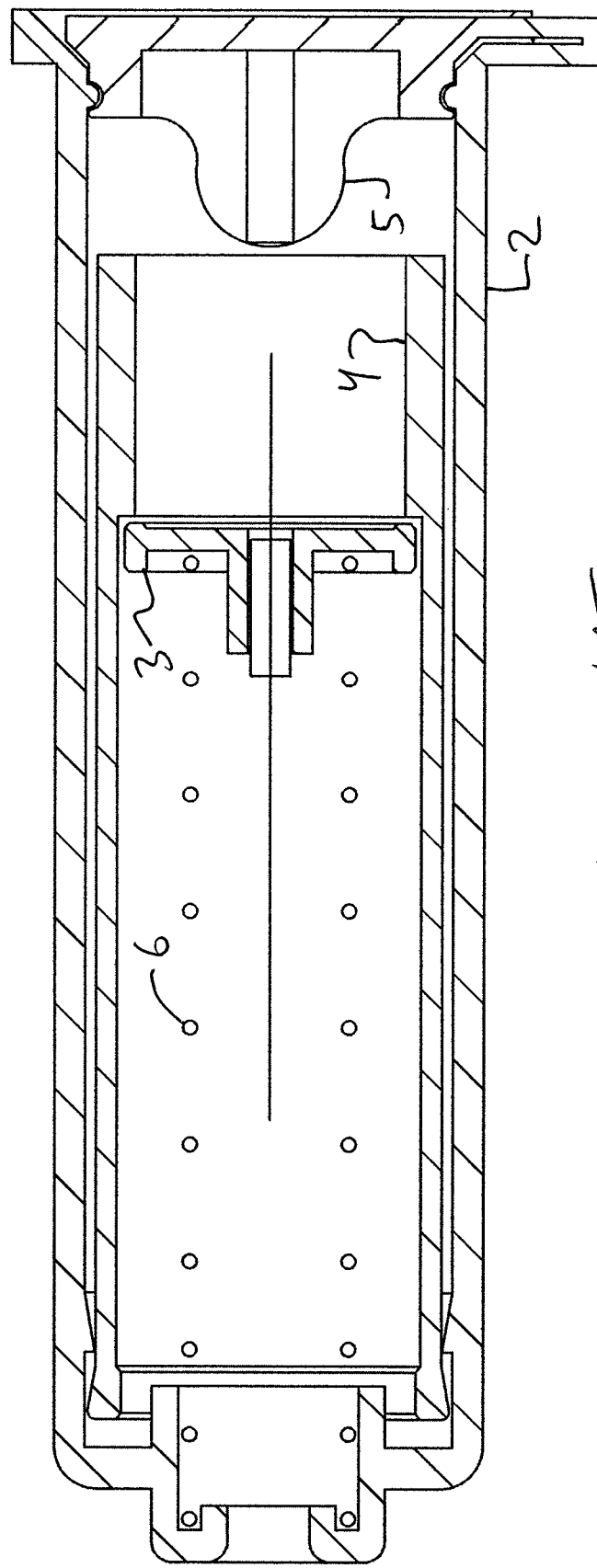
FIG. 4 shows a cross-section view of FIG. 1 after the cap is moved to the closed position and after the needle holding member is moved to the fully retracted position. The device can now be safely disposed of and handled because the double-ended needle which is mounted to the needle holding member if fully contained within the device and a user therefore cannot be accidentally pricked by the needle.
Figure 5:
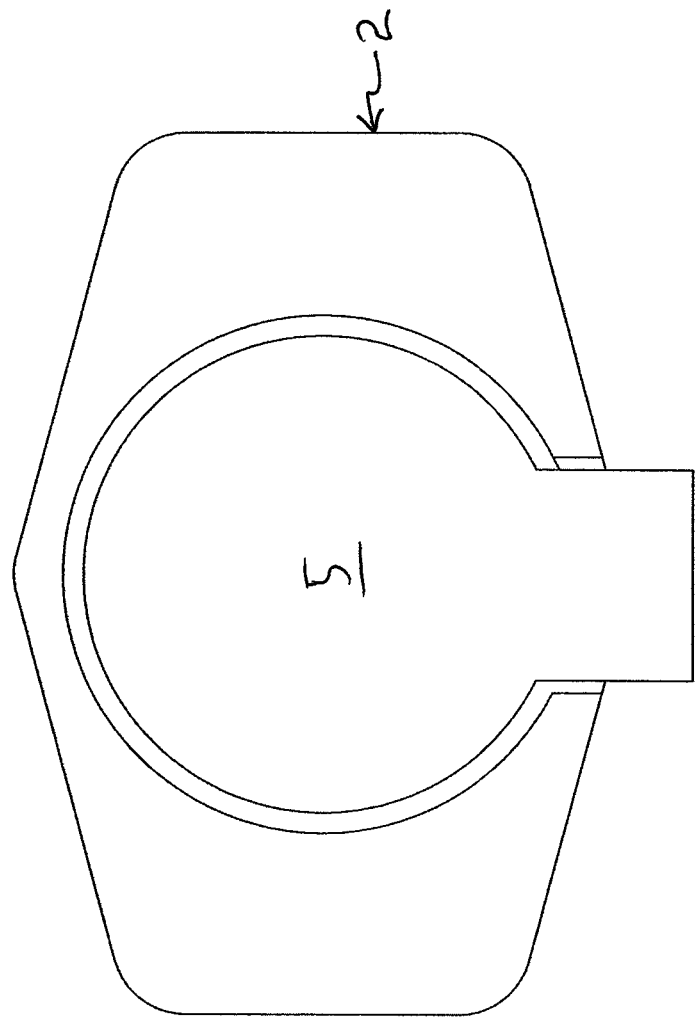
FIG. 5 shows a rear end view of FIG. 4.
Figure 6:
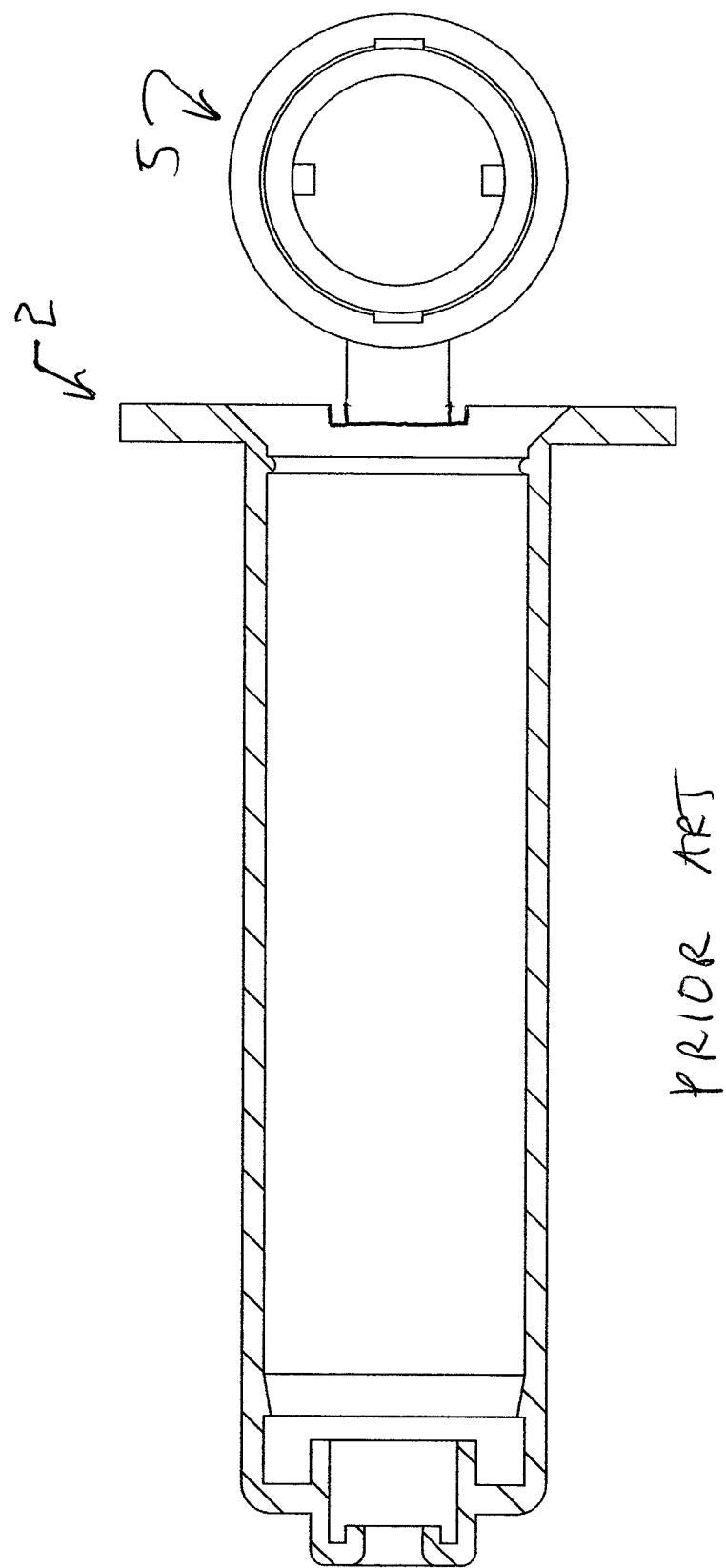
FIG. 6 shows a top cross-section view of the tubular outer body used in the embodiment shown in FIG. 1.
Figure 10:
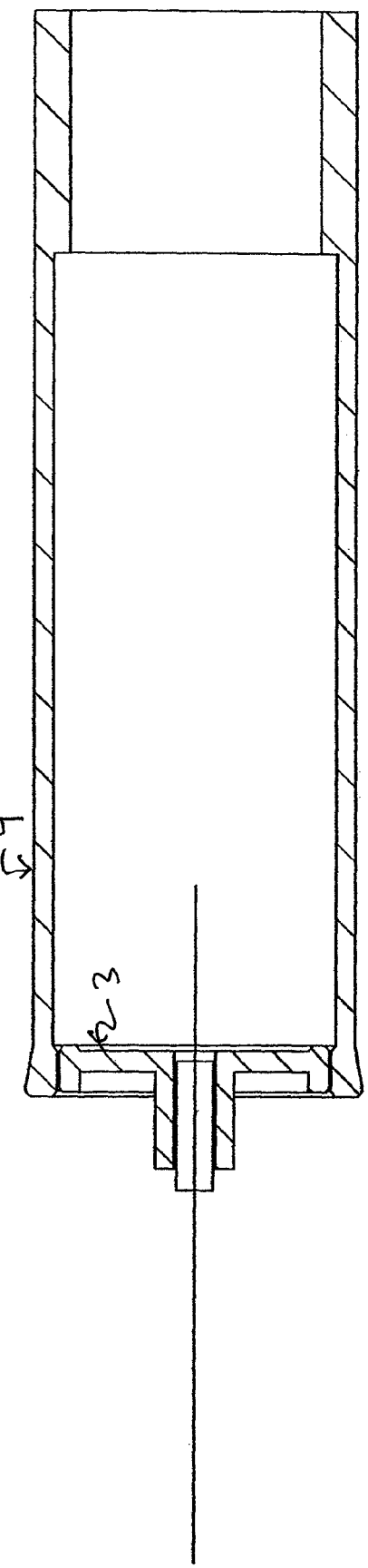
FIG. 10 shows a cross-section view of the movable member and the assembly shown in FIG. 8 mounted thereto and used in the embodiment shown in FIG. 1.

Referring now to the drawings and first to FIGS. 11-21 which shows a first non-limiting embodiment of a blood collection device 10 according to the invention. The device 10 includes a generally cylindrical outer sleeve or outer body member 20 which includes a proximal end 20a configured to allow an external needle N of a double-ended needle member or holder 30 to pass therethrough, and a distal end 20b which can be closed off by a cap 50. An inner flange IF is arranged at the proximal end 20a. The needle holder 30 has an outer circumferential surface OCS (see FIG. 15) which frictionally engages with an inner circumferential surface ICS (see FIGS. 13 and 18) of a proximal end of an inner sleeve 40. The surfaces ICS and OCS have generally corresponding shapes and need not be straight or cylindrical, i.e., they can also be, e.g., tapered or have an other non-straight shapes. The device 10 also includes a spring 60 which functions to move the needle holder 30 distally when the outer circumferential surface OCS of the needle holder 30 is released from frictional engagement with the inner circumferential surface ICS of the proximal end of the inner sleeve 40. As is evident from FIG. 12, once a user moves the cap 50 to the closed position, the sleeve 40 is caused to move axially in the proximal direction which, in turn, causes outer circumferential surface OCS of the needle holder 30 no longer frictionally engage with the inner circumferential surface ICS of the proximal end of the inner sleeve 40. The spring 60 is then free to move the needle holder 30 within the sleeve 40 in a distal direction which ensures that the needle holder 30 is fully and safely arranged within the device 10. The device can then be safely handled and discarded.

Figure 11:
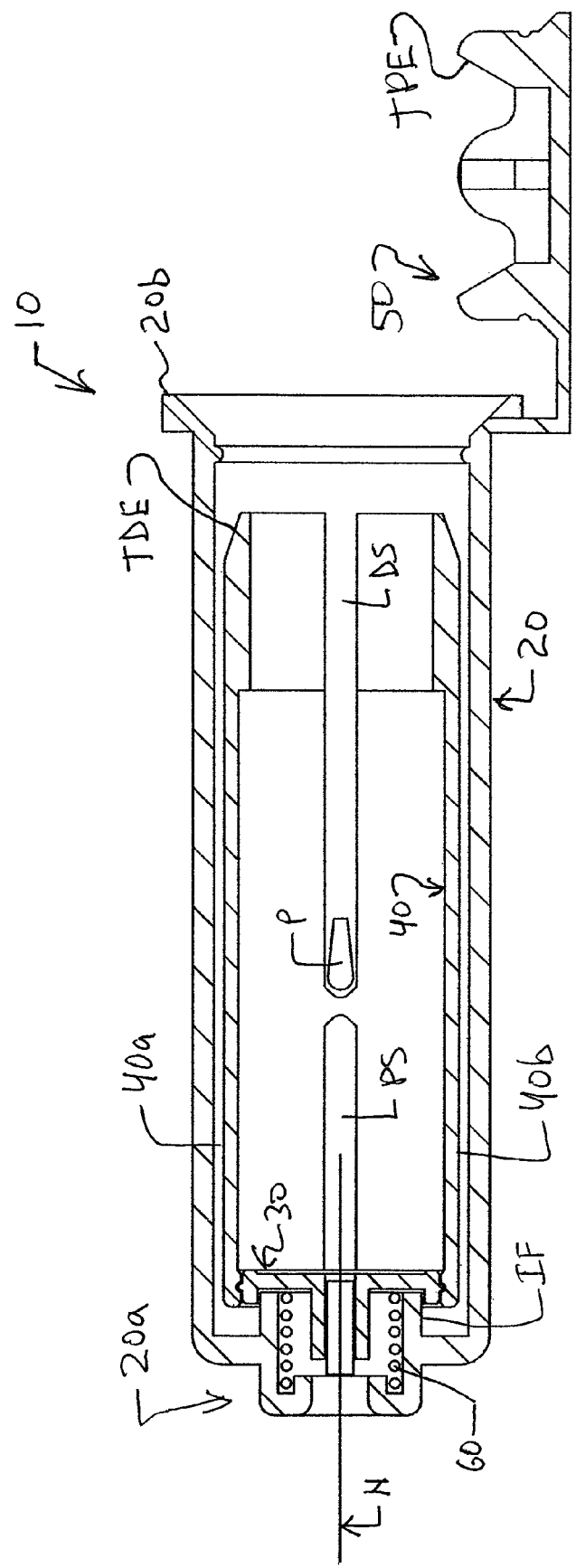
FIG. 11 shows a cross-section view of a blood collection device according to one embodiment of the invention. The device is shown in a prior-use or packaged position and is ready to receive therein a collection tube.
Figure 12:
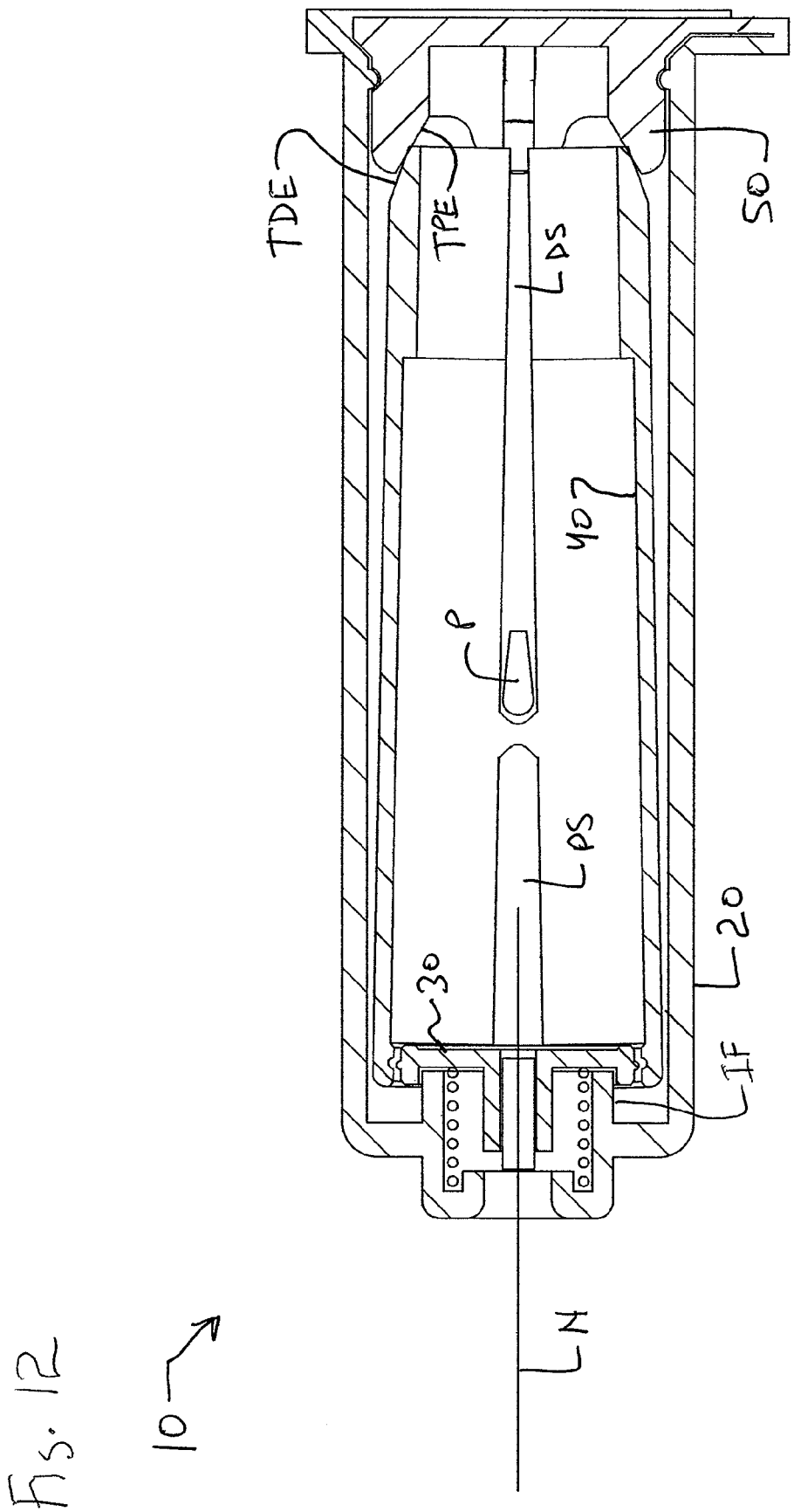
FIG. 12 shows a cross-section view of FIG. 11 after the cap is moved to the closed position and before the needle holding member is moved to the fully retracted position. This figure illustrates how the front of the movable member is cause to expand generally radially (thereby releasing its engagement with the needle holding member) by a radially contracting the rear end of the movable member with the aid of the cap.

The disengagement of the proximal end of the sleeve 40 from the needle holder 30 (see FIG. 12) functions as follows. The sleeve 40 is prevented from moving axially backwards within the body 20 by two oppositely arranged projections P, but is biased towards this direction by the spring 60 which FIG. 11 is substantially fully compressed. The projections P also function as static pivot points and allow the generally half-circular or arc-shaped sections 40a and 40b of the sleeve 40 to pivot relative each other. Thus, as shown in FIG. 12, when the distal ends of the generally half-circular or arc-shaped sections 40a and 40b of the sleeve 40 are moved towards each other, the proximal ends of the generally half-circular or arc-shaped sections 40a and 40b of the sleeve 40 are moved away from each other. As a result, the two oppositely arranged proximal slots PS widen while the two oppositely arranged distal slots DS narrow. As is shown in FIG. 12, this pivot movement is caused when the user moves the cap 50 to the closed position, and more specifically, when the inner tapered surfaces TPE of the cap 50 engage with tapered surfaces TDE of the sleeve 40 and force the tapered surfaces TDE of the sleeve 40 inwardly.

With reference to FIGS. 11 and 12, when the user moves the cap 50 to the closed position, the inner tapered surfaces TPE of the cap 50 engage with tapered surfaces TDE of the sleeve 40 and force the tapered surfaces TDE of the sleeve 40 inwardly. This, however, also causes the sleeve 40 to move a small amount in the distal direction, and this movement is not prevented by the projections P. Instead, this movement is limited by the biasing force of the spring 60 and by contact between a front-facing surface of the holder 30 and a rear-facing surface of the inner flange IF of the body 20.

Figure 13:
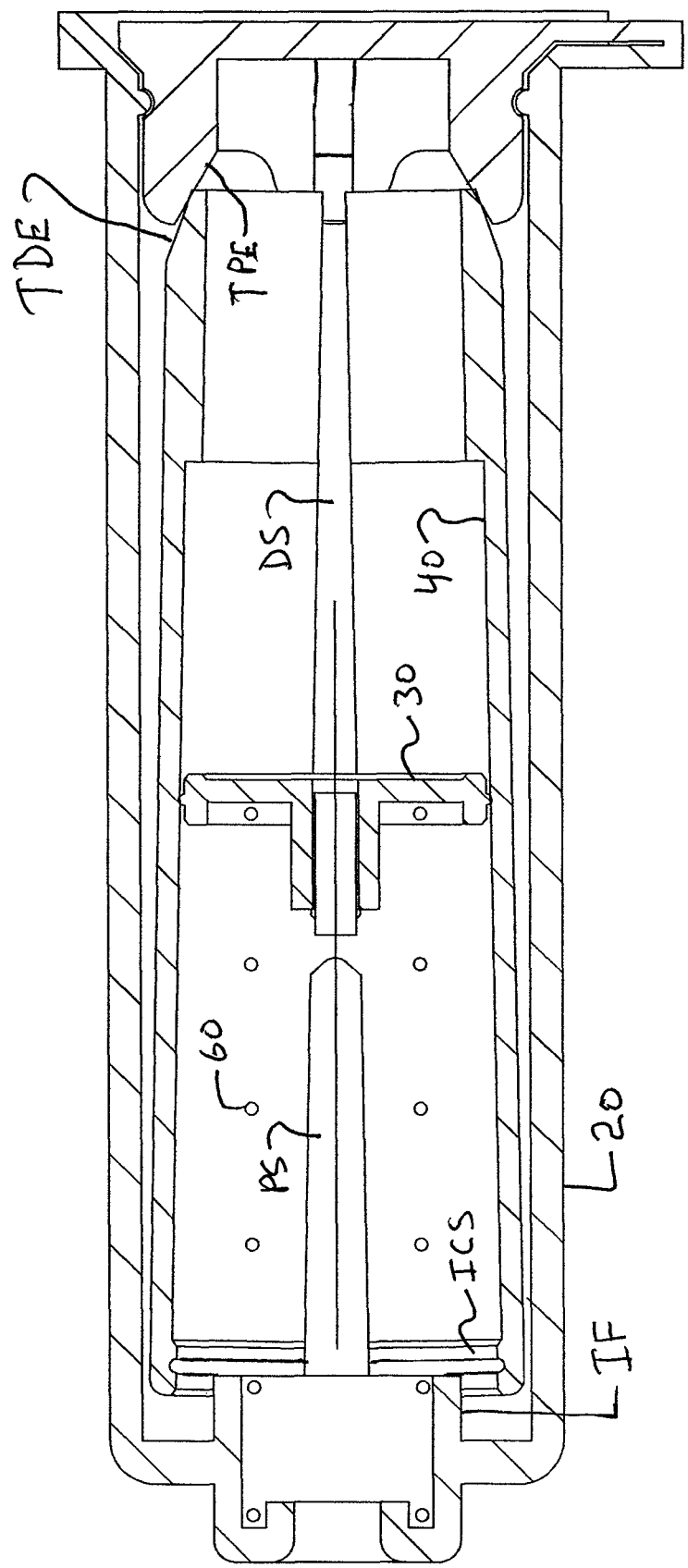
FIG. 13 shows a cross-section view of FIG. 11 after the cap is moved to the closed position and after the needle holding member is moved to the fully retracted position. The device can now be safely disposed of and handled because the double-ended needle which is mounted to the needle holding member if fully contained within the device and a user therefore cannot be accidentally pricked by the needle.

As is shown in FIG. 13, when the user moves the cap 50 to the closed position shown in FIG. 12, the pivoting movement of the sections 40a and 40b automatically causes the surface ICS to separate from the surface OCS. Since the frictional engagement between the surface ICS and the surface OCS constitutes the only engagement or connection between the holder 30 and the sleeve 40, the disengagement of these surfaces leaves the holder 30 free to move axially distally. Furthermore, because the spring 60 maintains a biasing force against the holder 30, when the engagement is released, the spring 60 will automatically expand axially and force the holder 30 to move distally within the sleeve 40. Thus, in turn, results in the needle N being retracted into the sleeve 40 and positions it safely within the body 20. The device 10 shown in FIG. 13 is now rendered unusable, i.e., cannot be reused, and can be safely handled and disposed of without fear of the needle causing injury to persons who handle the used device 10.

With reference to FIGS. 14-19, it can be seen that the sleeve 40 and the needle holder 30 constitute a sub-assembly with the generally half-circular or arc-shaped sections 40a and 40b of the sleeve 40 assuming a generally cylindrical shape. The two oppositely arranged connecting portions CP function as the only mechanism connecting together the arc-shaped sections 40a and 40b of the sleeve 40. As such, when the distal ends of these members 40a and 40b are moved towards each other, the connecting portions CP become deflected and/or slightly elastically deformed thereby allowing the proximal ends of the generally half-circular or arc-shaped sections 40a and 40b of the sleeve 40 to move away from each other. However, in the relaxed shown in FIG. 14, the connecting portions CP ensure that the surfaces OSC and ICS remain in engagement. In order to assemble the sub-assembly shown in FIG. 14, one need only move the tapered surfaces TDE of the members 40a and 40b towards each other to cause a widening of the slots PS (and simultaneously a narrowing of the slot DS), insert the holder 30 within the proximal end of the sleeve 40, and then remove the force applied to the surfaces TDE allowing the sleeve 40 to again assume a generally cylindrical shape shown in FIG. 14. Of course, proper insertion and connection of the holder 30 requires ensuring that the projections CPP, EPP (see FIGS. 16 and 17) are aligned with the circumferential groove G of the sleeve 40 (see FIG. 18).

Figure 14:
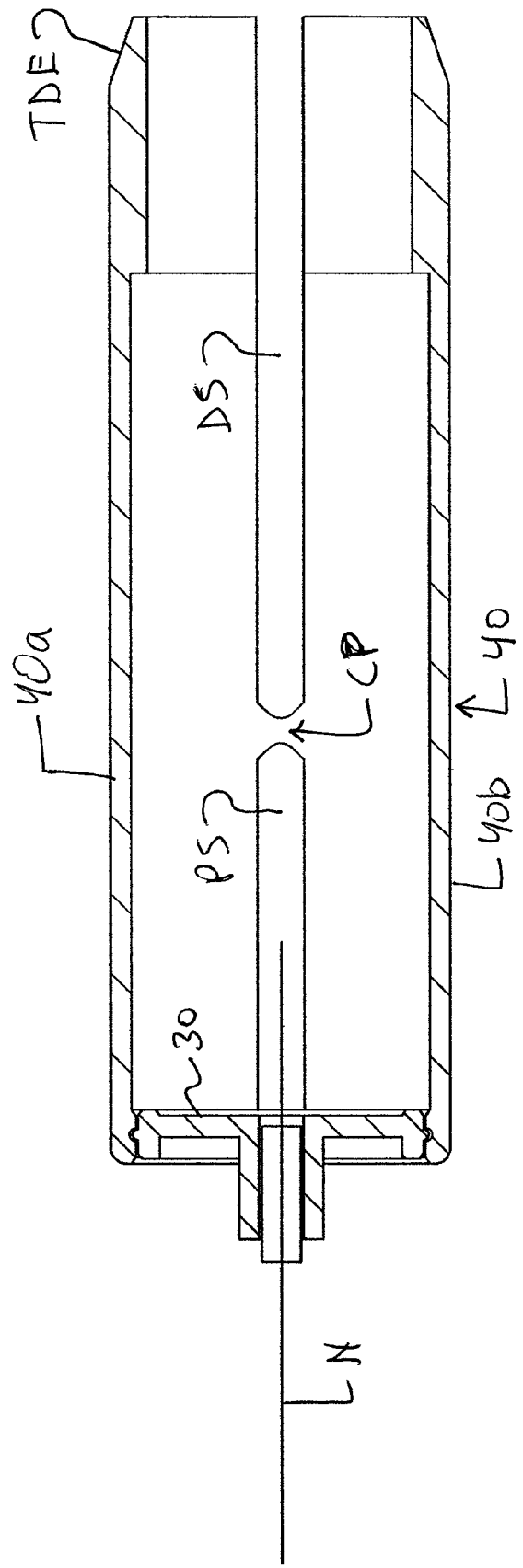
FIG. 14 shows a cross-section view of the movable member and the assembly shown in FIG. 15 mounted thereto and used in the embodiment shown in FIG. 11.
Figure 15:
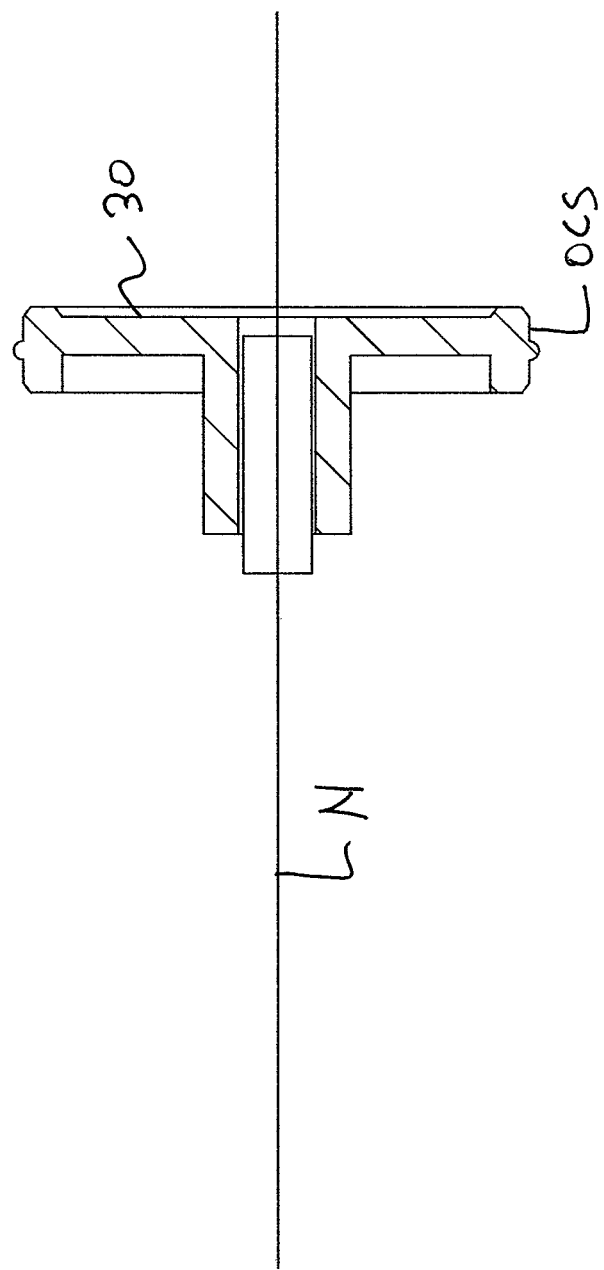
FIG. 15 shows a cross-section view of the needle holding member and a conventional type double-ended needle mounted thereto and used in the embodiment shown in FIG. 11.

The sub-assembly shown in FIG. 14 can be slid into the distal end of the body 20 in a relatively easy manner because the two integrally formed oppositely arranged projections P have a tapered inward facing surface which allows the connecting portions CP to slide over the projections P. The projections P also serve to align and/or guide the proper insertion movement of the sub-assembly shown in FIG. 14 as follows. Upon insertion of the sleeve 40 into the distal end of body 20, the user will align the proximal slots PS of the sleeve 40 with the projections P and then move the sleeve 40 axially in the proximal direction. Once the connecting portions CP of the sleeve 40 reach the projections P, the tapered surfaces of the projections P allow these portions CP to pass over the projections P until they pass the projections P and snap outwardly and assume the final position shown in FIG. 11. At this point, the rear-facing surface of the portions CP will abut the forward facing surface CSS (see FIG. 21) of the projections P. The spring 60 can, of course, be installed inside the body 20 in the same way as, e.g., the prior art device shown in FIGS. 1-10, and is preferably installed in the body 20 prior to or simultaneously with the insertion of the sub-assembly shown in FIG. 14.

Figure 16:
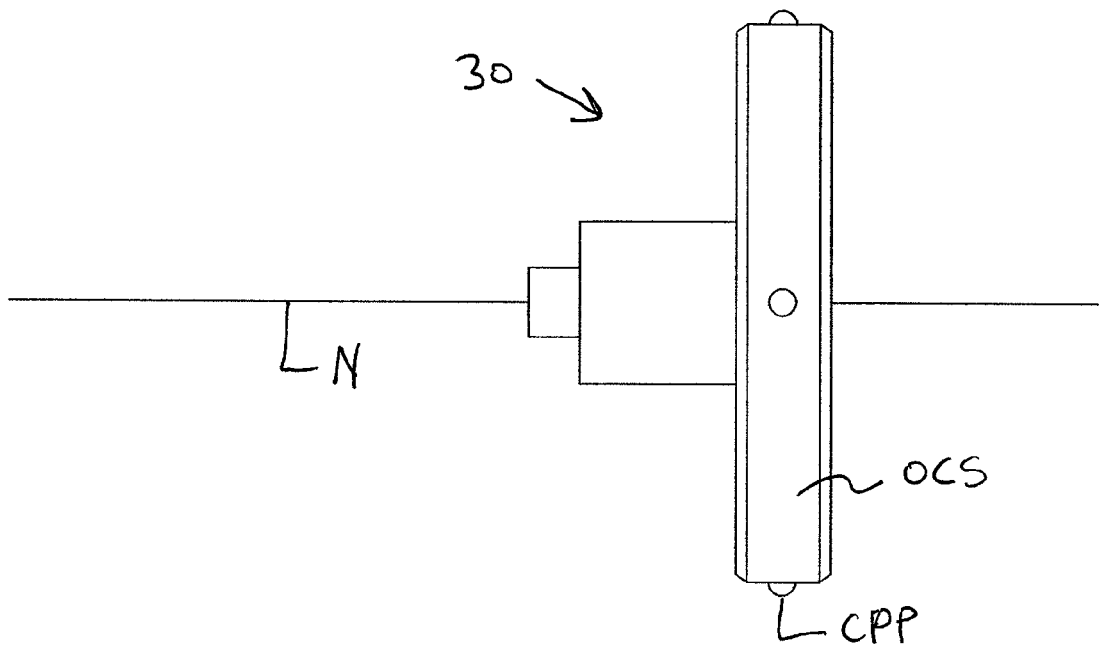
FIG. 16 shows a side view of another embodiment of a needle holding member with a conventional type double-ended needle mounted thereto and which can be used in the embodiment shown in FIG. 11.
Figure 17:
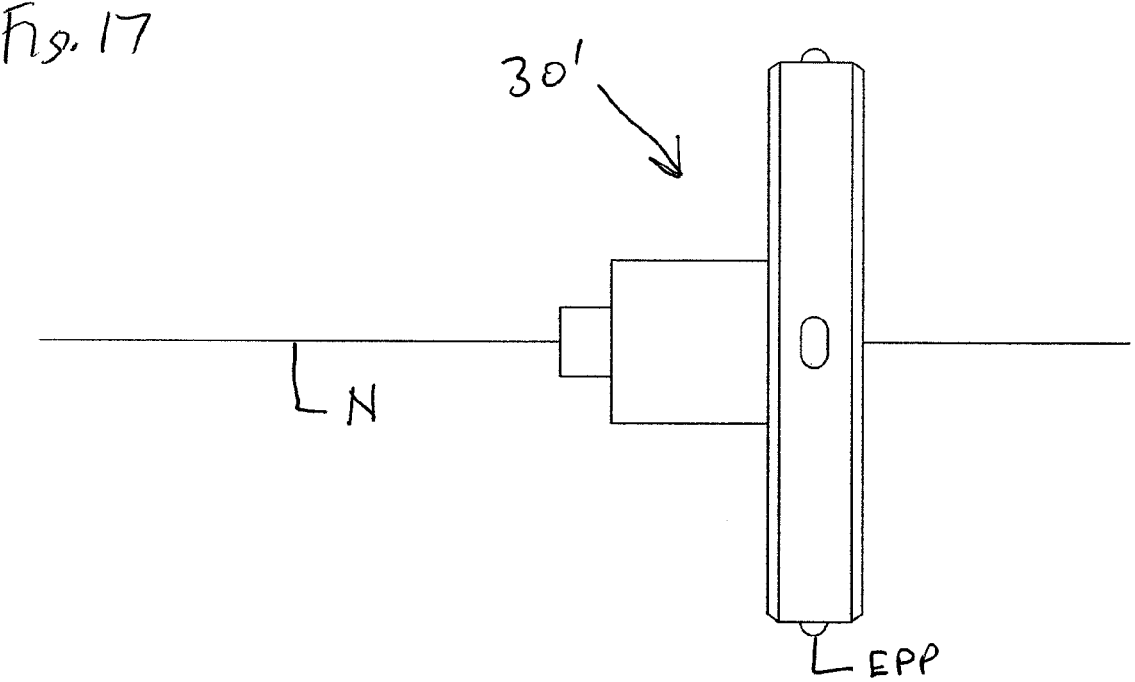
FIG. 17 shows a side view of still another embodiment of a needle holding member with a conventional type double-ended needle mounted thereto and which can be used in the embodiment shown in FIG. 11.
Figure 18:
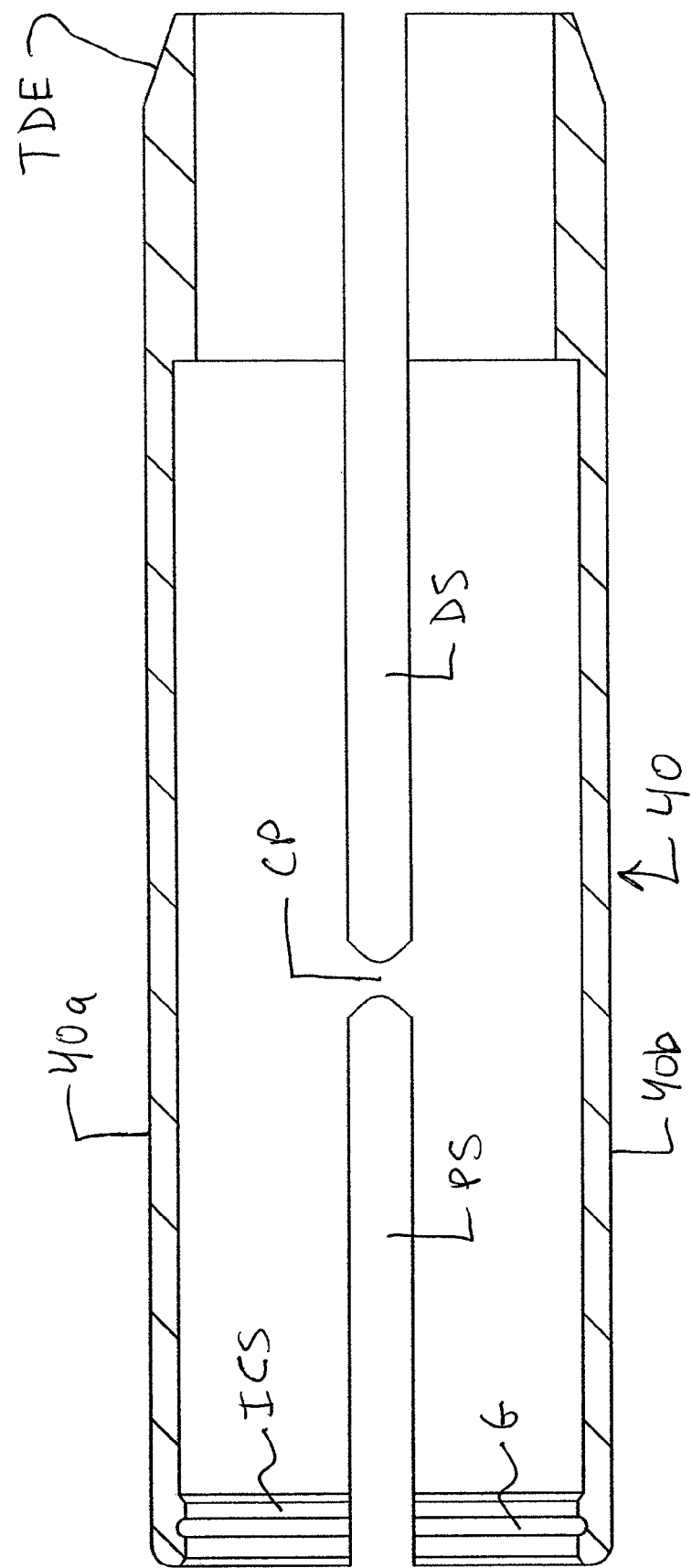
FIG. 18 shows a cross-section view of the movable member used in the embodiment shown in FIG. 11.
Figure 19:
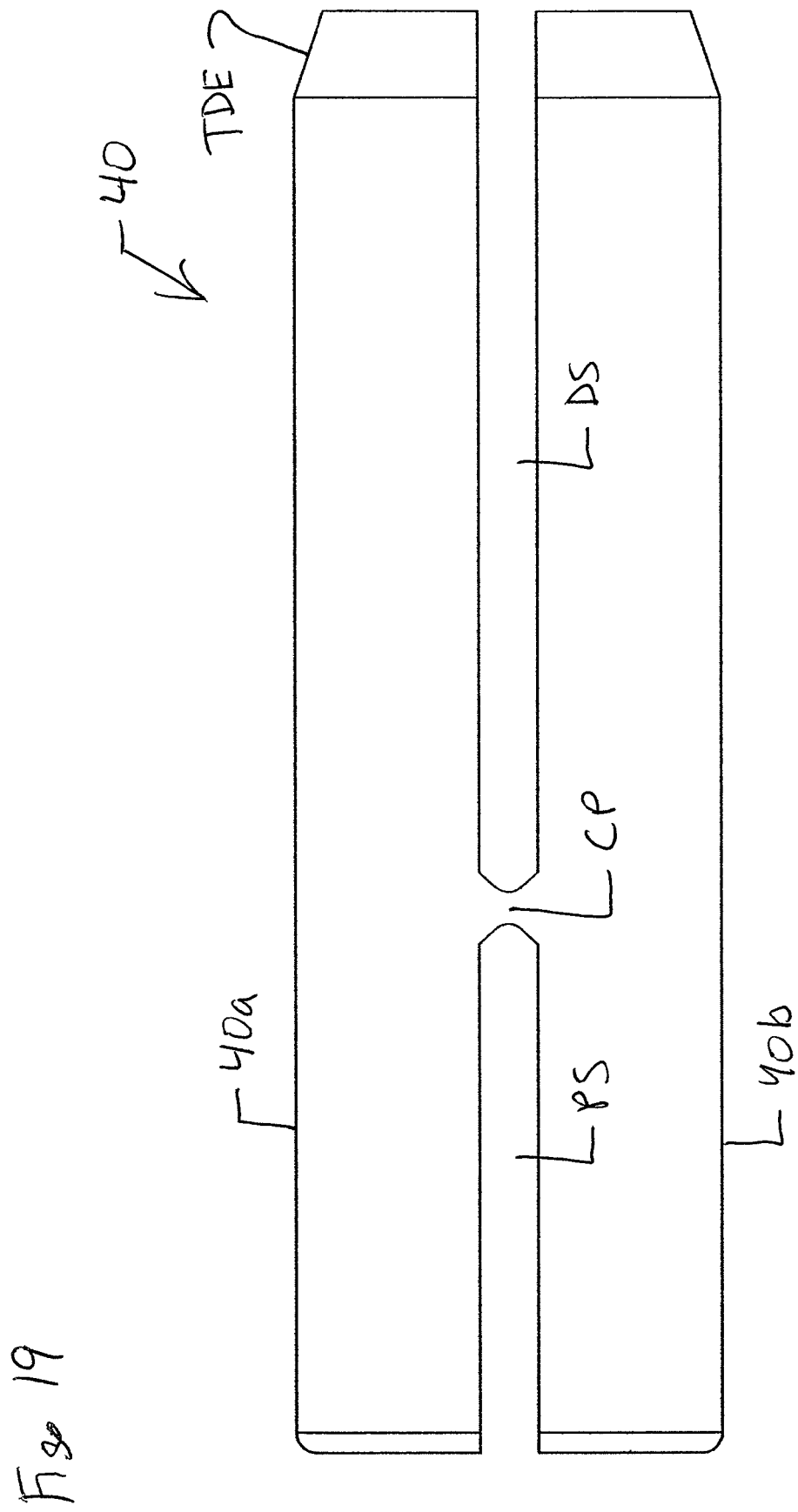
FIG. 19 shows a side view of FIG. 18.
Figure 20:
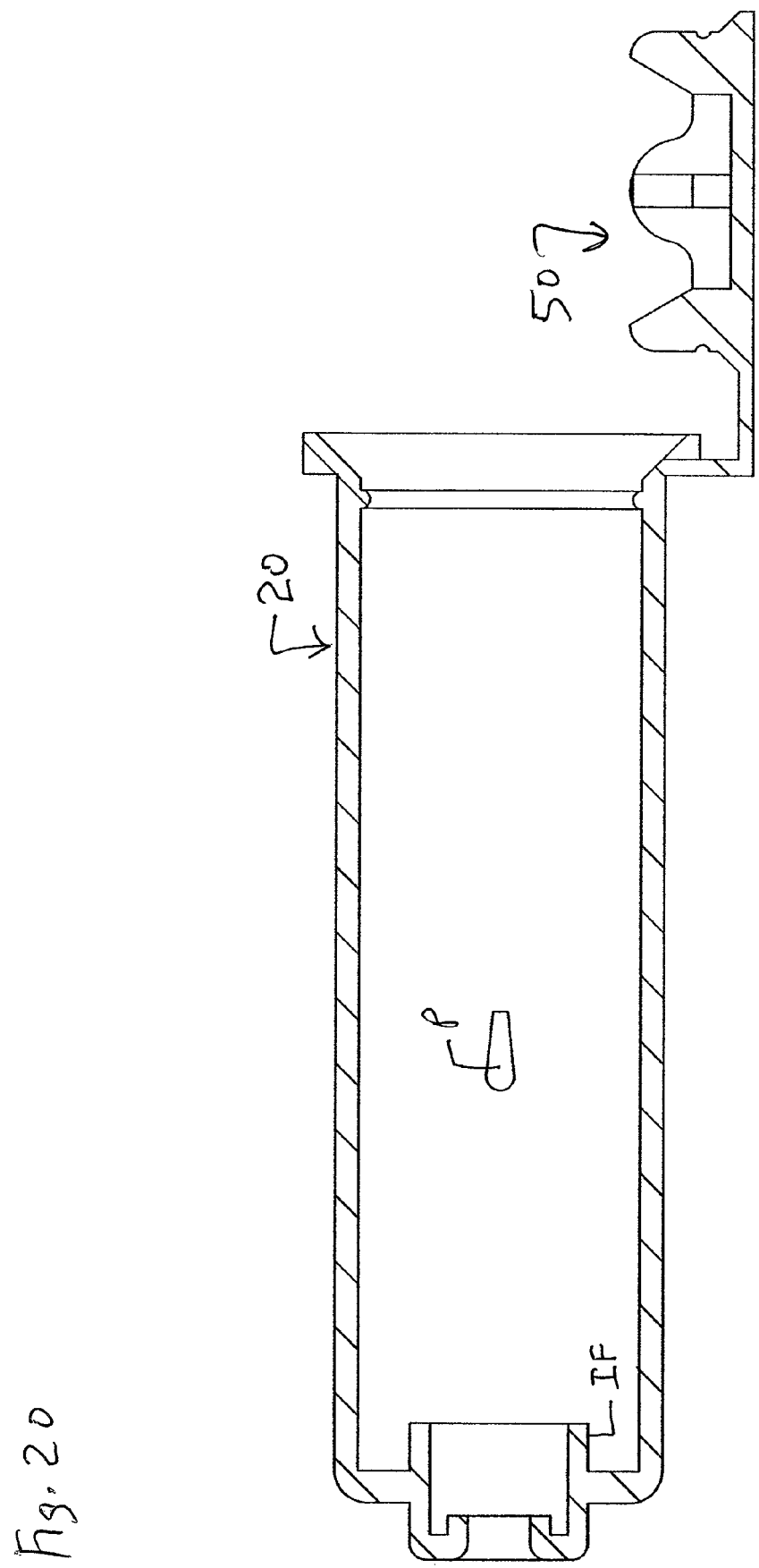
FIG. 20 shows a side cross-section view of the tubular outer body used in the embodiment shown in FIG. 11.
Figure 21:
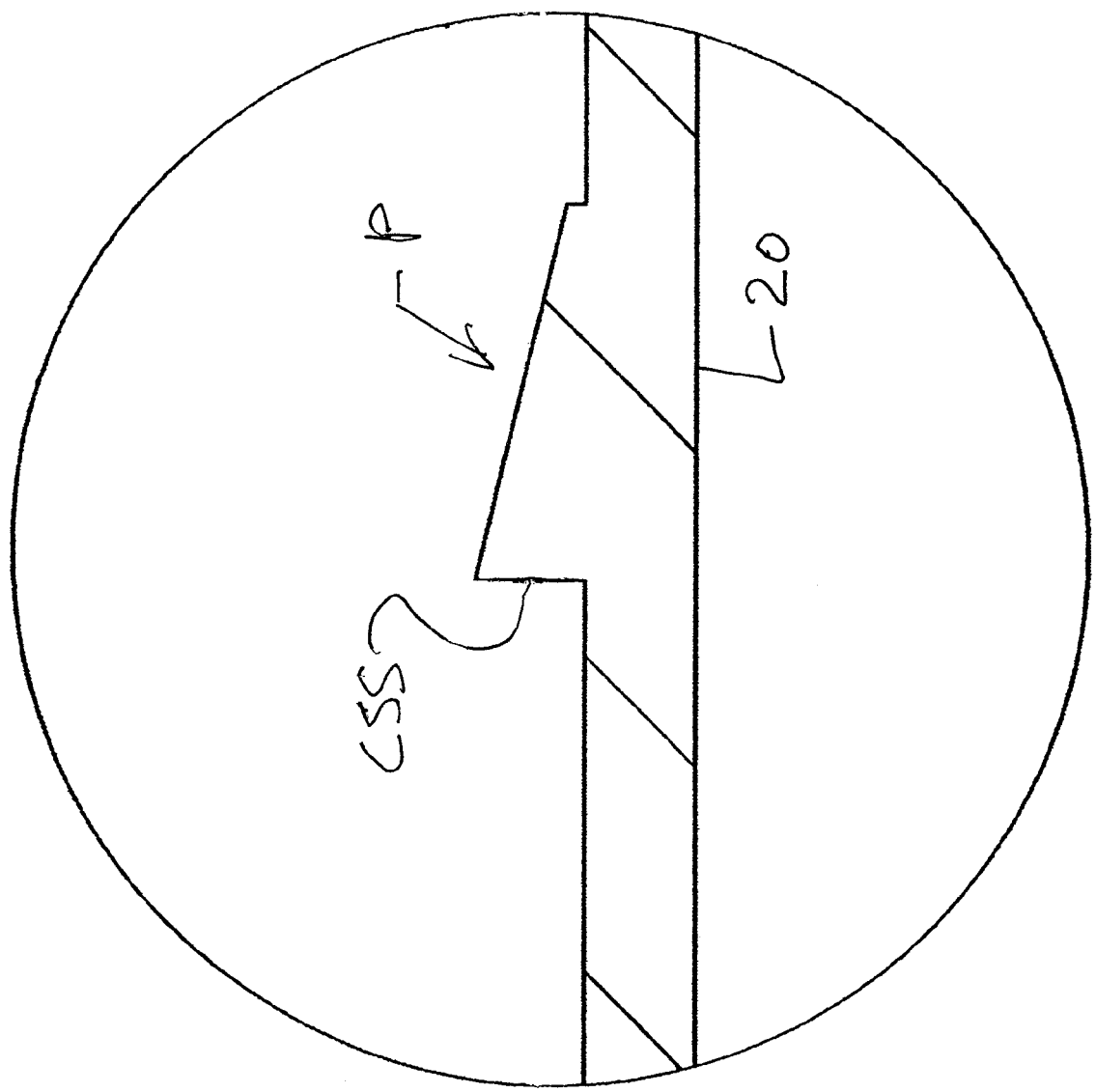
FIG. 21 shows an enlarged top cross-section view of a portion of the tubular outer body used in the embodiment shown in FIG. 1.

With reference to FIGS. 16-17, it can be seen that the needle holder 30 constitutes a sub-assembly having, in the case of FIG. 16, four equally angularly spaced circular projections CPP which are sized to engage or extend into the groove G of the sleeve 40. Of course, the invention also contemplates using as few as two oppositely arranged projections CPP. Furthermore, the projections CPP need not be circular and/or rounded and can be any shape (e.g., square, triangular, oval, polygonal, etc.) which securely and releasably engages with the groove G. Furthermore, the groove G need not correspond in shape to that of the projections CPP, and can similarly have any shape which securely and releasably engages with the projections CPP. By way of non-limiting example FIG. 17 shows four equally angularly spaced elongated projections EPP which are sized to engage or extend into the groove G of the sleeve 40. Again, the invention also contemplates using as few as two oppositely arranged projections EPP. Furthermore, the projections EPP need not be rounded and can be any shape (e.g., square, triangular, oval, polygonal, etc.) which securely and releasably engages with the groove G. The invention also contemplates other mechanisms for providing a releasable engagement between the surfaces OCS and ICS. Still further, instead of merely utilizing a single groove G and a single set of projections CPP, EPP, the invention also contemplates using two or more axially spaced grooves G and two or more axially spaced sets of projections CPP, EPP.

Figure 22:
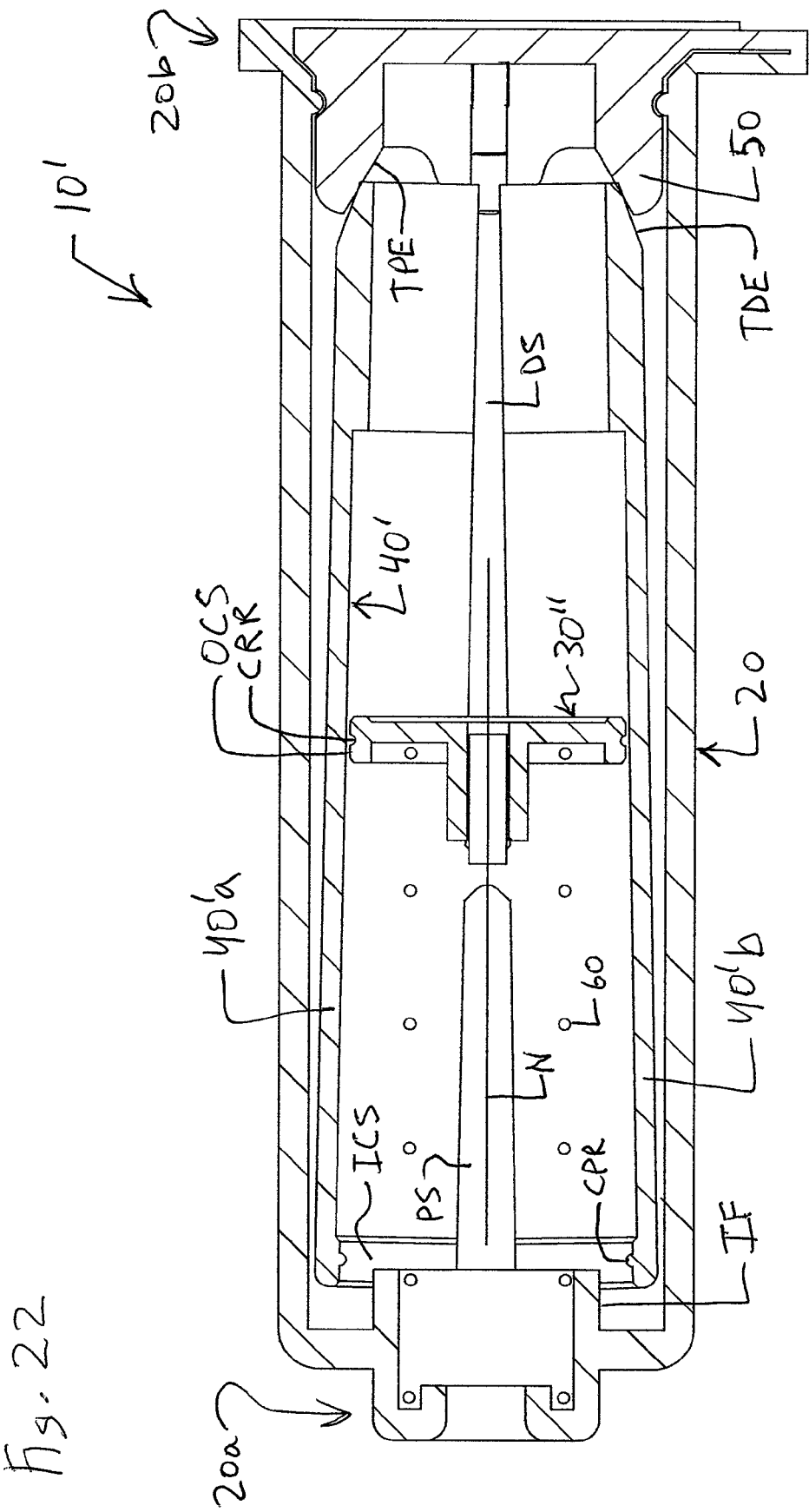
FIG. 22 shows a cross-section view of another embodiment of the blood collection device. The device is identical to that of FIG. 11 except that the movable member utilizes spaced apart projections and the needle holding member utilizes a circumferential recess.

FIG. 22 shows a second non-limiting embodiment of a blood collection device 10' according to the invention. The device 10' is shown in the used or post use position. As was the case in the previous embodiment, the device 10' includes a generally cylindrical outer sleeve or outer body member 20 which includes a proximal end 20a configured to allow an external needle N of a double-ended needle member or holder 30" to pass therethrough, and a distal end 20b which can be closed off by a cap 50. An inner flange IF is arranged at the proximal end 20a. The needle holder 30" has an outer circumferential surface OCS which frictionally engages with an inner circumferential surface ICS of a proximal end of an inner sleeve 40'. The surfaces ICS and OCS have generally corresponding shapes and need not be straight or cylindrical, i.e., they can also be, e.g., tapered or have an other non-straight shapes. The device 10' also includes a spring 60 which functions to move the needle holder 30" distally when the outer circumferential surface OCS of the needle holder 30" is released from frictional engagement with the inner circumferential surface ICS of the proximal end of the inner sleeve 40'. As was the case in the previous embodiment, once a user moves the cap 50 to the closed position, the sleeve 40' is caused to move axially in the proximal direction which, in turn, causes outer circumferential surface OCS of the needle holder 30" no longer frictionally engage with the inner circumferential surface ICS of the proximal end of the inner sleeve 40'. The spring 60 is then free to move the needle holder 30" within the sleeve 40' in a distal direction which ensures that the needle holder 30" is fully and safely arranged within the device 10'. This is shown in FIG. 22. The device can then be safely handled and discarded.

The disengagement of the proximal end of the sleeve 40' from the needle holder 30" functions as follows. The sleeve 40' is prevented from moving axially backwards within the body 20 by two oppositely arranged projections P (not shown, but similar to the previous embodiment), but is biased towards this direction by the spring 60. As in the previous embodiment, the projections P also function as static pivot points and allow the generally half-circular or arc-shaped sections 40'a and 40'b of the sleeve 40' to pivot relative each other. Thus, as shown in FIG. 22, when the distal ends of the generally half-circular or arc-shaped sections 40'a and 40'b of the sleeve 40' are moved towards each other, the proximal ends of the generally half-circular or arc-shaped sections 40'a and 40'b of the sleeve 40' are moved away from each other. As a result, the two oppositely arranged proximal slots PS widen while the two oppositely arranged distal slots DS narrow. As is shown in FIG. 22, this pivot movement is caused when the user moves the cap 50 to the closed position, and more specifically, when the inner tapered surfaces TPE of the cap 50 engage with tapered surfaces TDE of the sleeve 40' and force the tapered surfaces TDE of the sleeve 40' inwardly.

As is evident from FIG. 22, when the user moves the cap 50 to the closed position shown in FIG. 22, the pivoting movement of the sections 40'a and 40'b automatically causes the surface ICS to separate from the surface OCS. Since the frictional engagement between the surface ICS and the surface OCS constitutes the only engagement or connection between the holder 30" and the sleeve 40', the disengagement of the surfaces ICS and OCS leaves the holder 30" free to move axially in the distal direction. Furthermore, because the spring 60 maintains a biasing force against the holder 30", when the engagement is released, the spring 60 will automatically expand axially and force the holder 30" to move distally within the sleeve 40'. Thus, in turn, results in the needle N being retracted into the sleeve 40' and positions it safely within the body 20. The device 10' shown in FIG. 22 is now rendered unusable, i.e., cannot be reused, and can be safely handled and disposed of without fear of the needle causing injury to persons who handle the used device 10'.

In the embodiment shown in FIG. 22, the needle holder 30" has two equally angularly spaced circular indentations or blind recesses CRR which are sized to receive therein and engage with corresponding projections CPR of the sleeve 40'. Of course, the invention also contemplates using more than two oppositely arranged projections CPR and recesses CRR. Additionally, it is possible, and even preferable from a manufacturing or assembly standpoint, to utilize a continuous or circumferential groove in place of the two recesses CRR. Furthermore, the projections CPR need not be circular and/or rounded and can be any shape (e.g., square, triangular, oval, polygonal, etc.) which securely and releasably engages with the recesses CRR. Furthermore, the recess CRR need not correspond in shape to that of the projections CPR, and can similarly have any shape which securely and releasably engages with the projections CPR. Other than the different configurations shown in FIG. 22 regarding the surfaces ICS and OCS, the embodiment shown in FIG. 22 is substantially similar to that of FIGS. 11-21.

Figure 23:
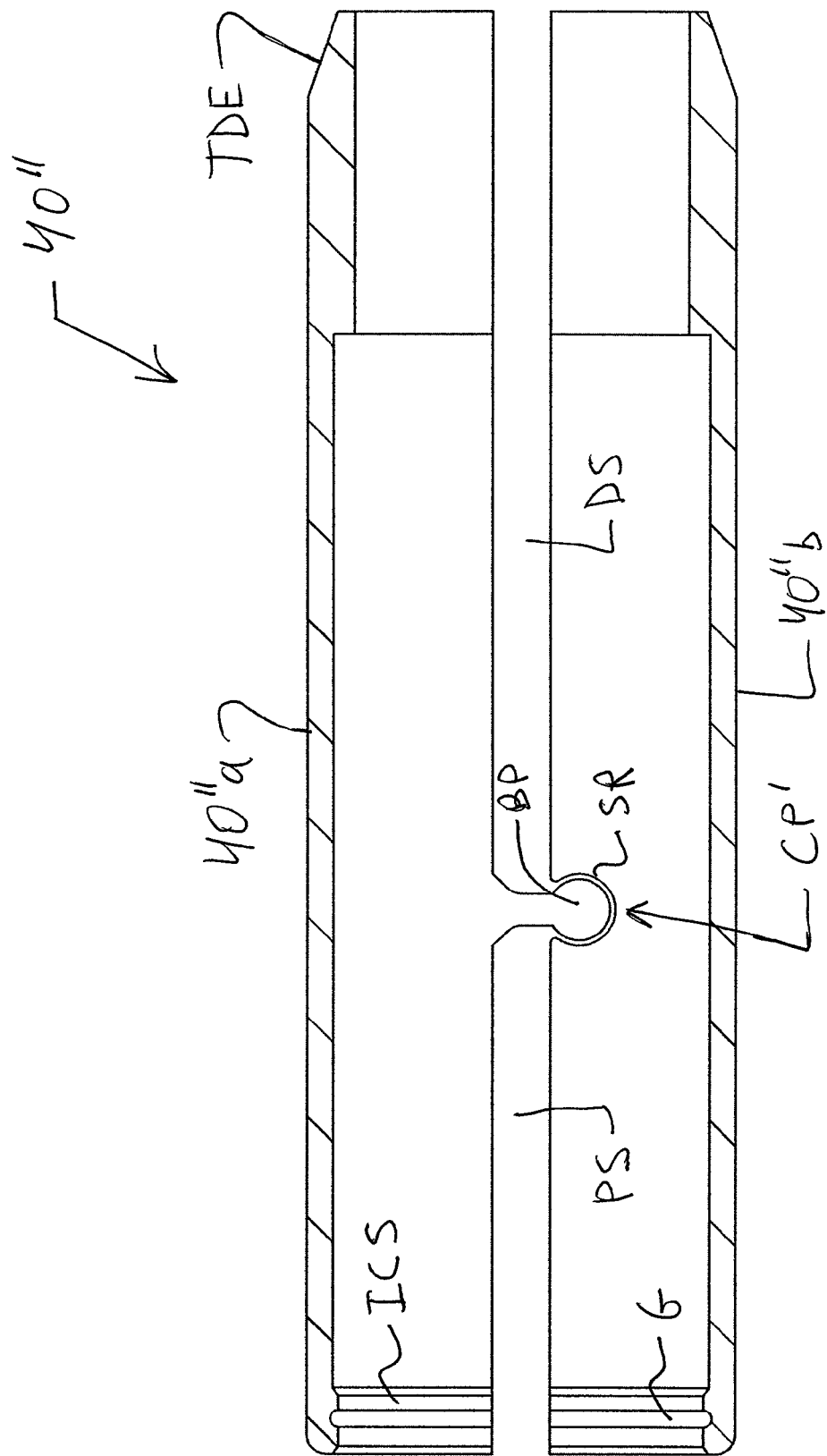
FIG. 23 shows a side cross-section view of another embodiment of a movable member which can be used in the embodiment shown in FIG. 11.

FIG. 23 shows another embodiment of an inner sleeve 40" which can be used, e.g., in the embodiment of FIGS. 11-21 in place of the sleeve 40. The sleeve 40" is similar to sleeve 40 except that the connecting portions CP' in the instant embodiment is formed by a sideways disconnectable joint formed by circular projection BP and a socket recess SR which forms a pivot bearing for the projection BP. The advantage of this joint CP' system is that it allows arc-shaped members 40"a and 40"b forming the sleeve 40" to pivot relative to each other more easily, i.e., when the cap 50 is moved to the closed position and the tapered surfaces TPE engage the tapered surfaces TDE. Another advantage is that the arc-shaped members 40"a and 40"b forming the sleeve 40" can be formed separately and allows the sleeve 40" and the holder 30 to be assembled more easily.

Figure 24:
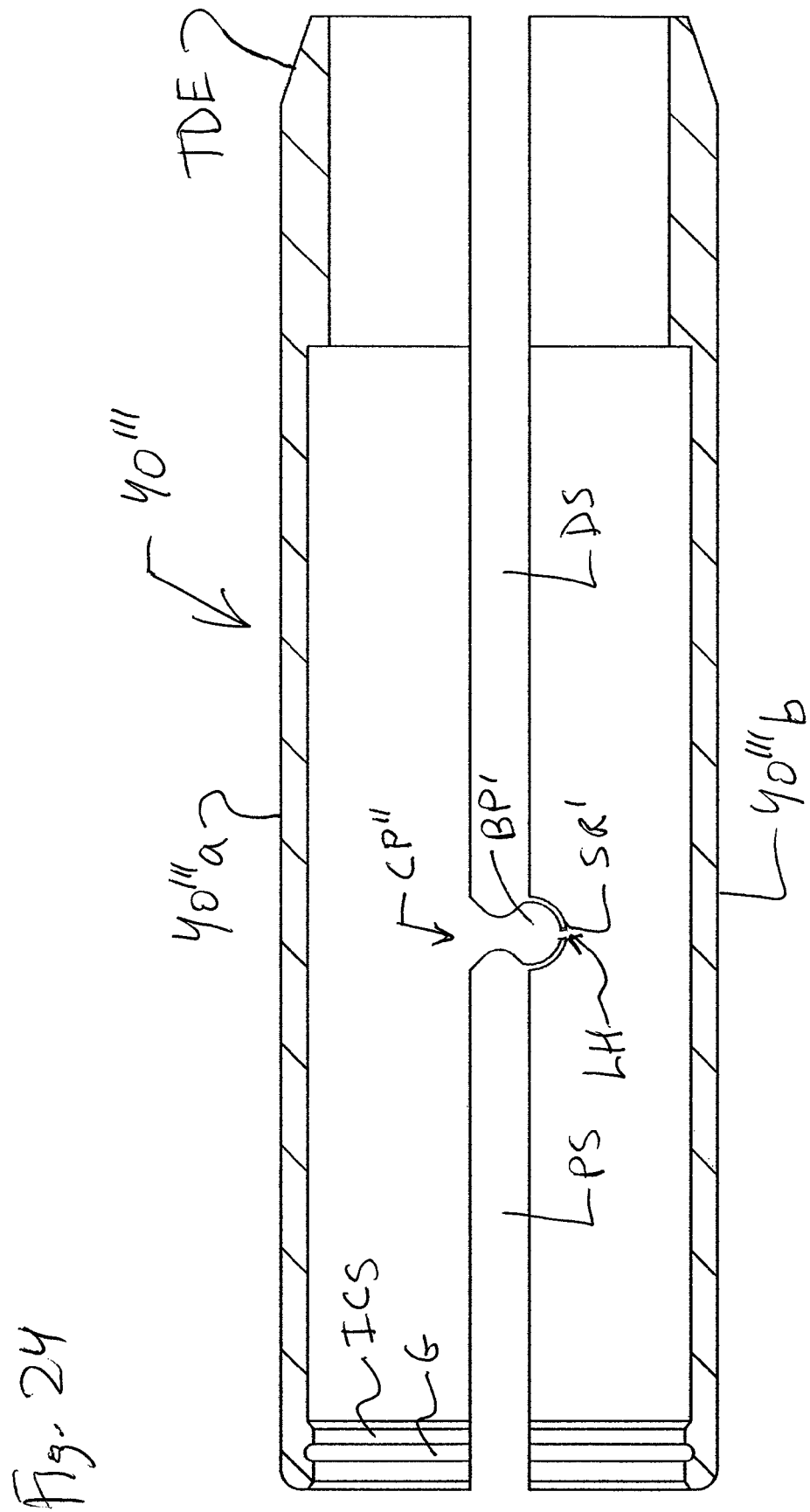
FIG. 24 shows a side cross-section view of still another embodiment of a movable member which can be used in the embodiment shown in FIG. 11.

FIG. 24 shows another embodiment of an inner sleeve 40''' which can be used, e.g., in the embodiment of FIGS. 11-21 in place of the sleeve 40. The sleeve 40''' is similar to sleeve 40 except that the connecting portions CP'' in the instant embodiment is formed by a joint formed by circular projection BP' and a socket recess SR' which forms a pivot bearing for the projection BP'. The circular projection BP' and the socket recess SR' are connected to each other via a small connecting band which forms a living hinge LH. The advantage of this joint CP'' system is that it allows arc-shaped members 40'''a and 40'''b forming the sleeve 40''' to pivot relative to each other more easily, i.e., when the cap 50 is moved to the closed position and the tapered surfaces TPE engage the tapered surfaces TDE. As was the case in the embodiment of FIG. 11, the sleeve 40''' is a one-piece member with arc-shaped members 40'''a and 40'''b connected to each other via the two living hinges LH.

FIGS. 25-29 show another non-limiting embodiment of a blood collection device 100 according to the invention. The device 100 includes a generally cylindrical outer sleeve or outer body member 200 which includes a proximal end 200*a* configured to allow an external needle N of a double-ended needle member or holder 300 to pass therethrough, and a distal end 200*b* which can be closed off by a cap 500. An inner flange IF is arranged at the proximal end 200*a*. The needle holder 300 has an outer circumferential surface OCS (see FIG. 27) which frictionally engages with an inner circumferential surface ICS (see FIG. 28) of a proximal end of an inner sleeve 400. The surfaces ICS and OCS have generally corresponding shapes and need not be straight or cylindrical, i.e., they can also be, e.g., tapered or have an other non-straight shapes. The device 100 also includes a spring 600 which functions to move the needle holder 300 distally when the outer circumferential surface OCS of the needle holder 300 is released from frictional engagement with the inner circumferential surface ICS of the proximal end of the inner sleeve 400. Once a user moves the cap 500 to the closed position, the sleeve 400 is caused to move axially in the proximal direction which, in turn, causes outer circumferential surface OCS of the needle holder 300 no longer frictionally engage with the inner circumferential surface ICS of the proximal end of the inner sleeve 400. The spring 600 is then free to move the needle holder 300 within the sleeve 400 in a distal direction which ensures that the needle holder 300 is fully and safely arranged within the device 100. The device can then be safely handled and discarded.

Figure 25:
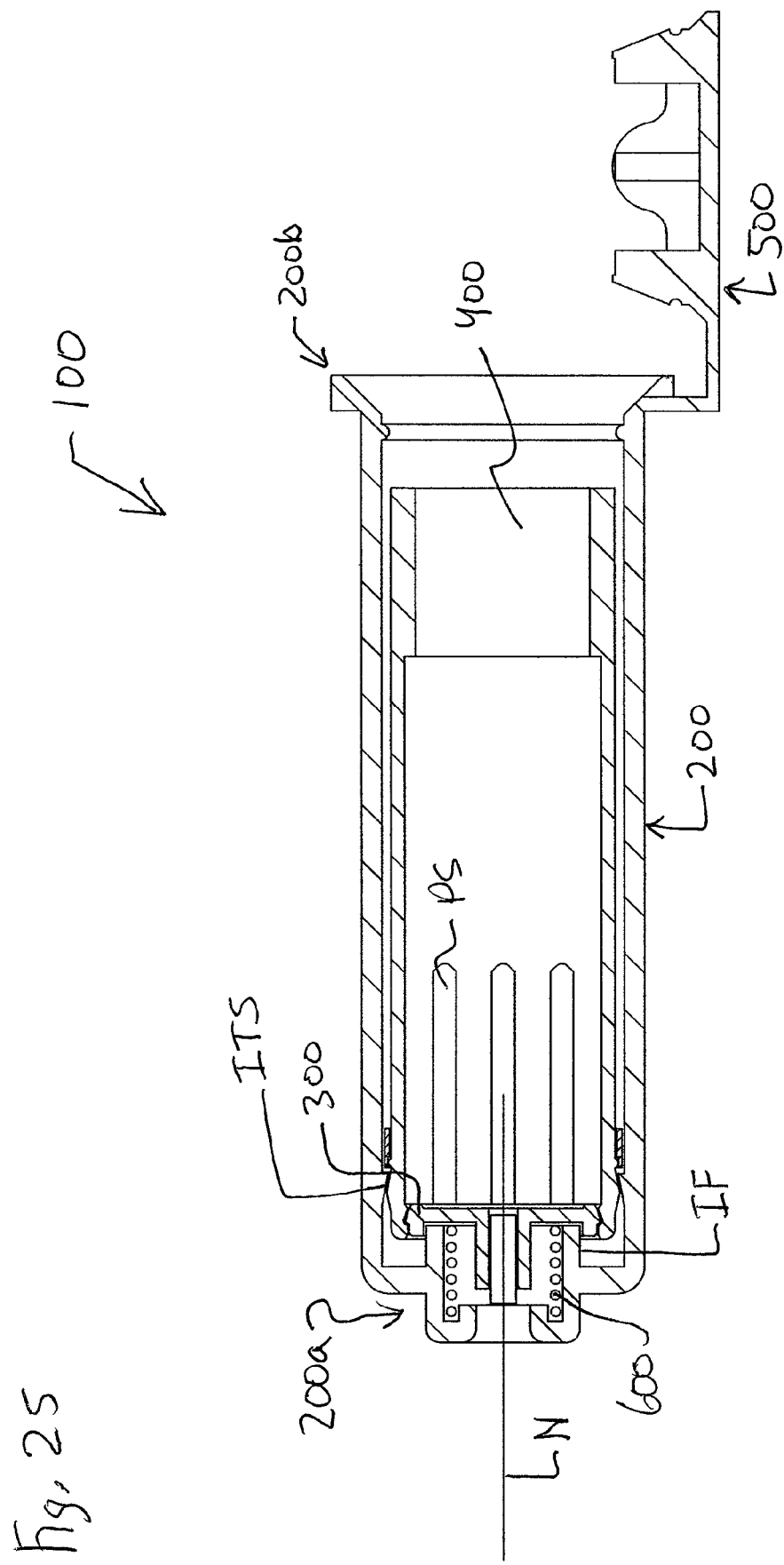
FIG. 25 shows a cross-section view of still another embodiment of the blood collection device. The device utilizes an axially movable ring which, when moved distally, allows the front or proximal end of the movable member to expand radially when the movable member moves relative to the needle holding member. This would occur when the cap is moved to the closed position.

The disengagement of the proximal end of the sleeve 400 from the needle holder 300 functions as follows. The sleeve 400 is prevented from moving axially backwards within the body 200 by a circumferential tapered shoulder TS engaging an inner tapered shoulder ITS of the body 200, but is biased towards this direction by the spring 600 which, in FIG. 25, is substantially fully compressed. The sleeve 400 has a plurality of proximal slots PS which divide the proximal end of the sleeve 400 into a plurality of spring fingers each having a portion of the surface ICS. A ring-shaped retaining sleeve RSS is movably mounted to the sleeve 400 and is movable between the locked position shown in FIGS. 25 and 26, and an unlocked position characterized by movement of the ring RSS in the distal direction or movement of the sleeve 400 in the proximal direction while the sleeve RSS remains static (similar to that shown in FIG. 30. When the sleeve 400 is moved in the proximal direction by the closing of the cap 500, the sleeve RSS contacts an annular surface the tapered shoulder ITS preventing the sleeve RSS from further movement in the proximal direction. The sleeve 400, however, continues to move in the proximal direction. When a point is reach where the sleeve RSS is moved sufficiently to the unlocked position, the spring fingers formed by the proximal slots PS are free to expand radially thereby releasing the engagement between the surface ICS of the sleeve 400 and the surface OCS of the holder 300. As a result, the proximal slots PS widen. This movement of the sleeve 400 and disengagement of the surfaces ICS and OCS is caused to occur automatically when the user moves the cap 500 to the closed position, and more specifically, when an annular surface or proximal end of cap 500 contacts an annular surface or distal end of the sleeve 400 and forces the sleeve 400 to move axially in the proximal direction.

Thus, when the user moves the cap 500 to the closed position (not shown), axial movement of the sleeve 400 and movement of the sleeve RSS relative to the sleeve 400 automatically causes the surface ICS to separate from the surface OCS. Since the frictional engagement between the surface ICS and the surface OCS constitutes the only engagement or connection between the holder 300 and the sleeve 400, the disengagement of these surfaces leaves the holder 300 free to move axially distally. Furthermore, because the spring 600 maintains a biasing force against the holder 300, when this engagement is released, the spring 600 will automatically expand axially and force the holder 300 to move distally within the sleeve 400. This, in turn, results in the needle N being retracted into the sleeve 400 and positions it safely within the body 200. The device 100 is then rendered unusable, i.e., cannot be reused, and can be safely handled and disposed of without fear of the needle causing injury to persons who handle the used device 100.

Figure 26:
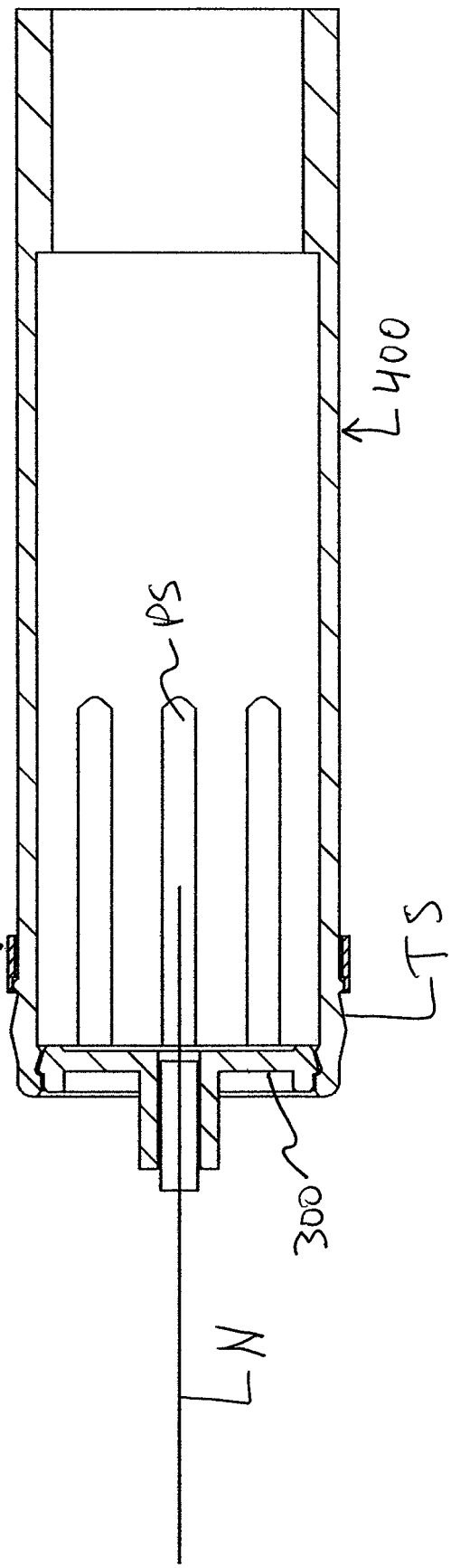
FIG. 26 shows a cross-section view of the movable member and the assembly shown in FIG. 27 mounted thereto and used in the embodiment shown in FIG. 25.

With reference to FIGS. 26-29, it can be seen that the sleeve 400, the retaining sleeve RSS, and the needle holder 300 constitute a sub-assembly. The proximal end of the sleeve 400 forms a plurality of arc-shaped sections or fingers divided by equally spaced slots PS. As such, these fingers are free to deflect outwardly or to slightly elastically deformed outwardly. However, the sleeve RSS functions to prevent this movement and ensures that the fingers are pressed tightly against the holder 300, and more specifically, that the surfaces OSC and ICS remain in engagement until the sleeve RSS is moved to a position which allows the fingers to deflect outwardly. In order to assemble the sub-assembly shown in FIG. 26, one need only slide the holder 300 into the proximal end of the sleeve 400 and thereafter slide the sleeve RSS onto the distal end of the sleeve 400 and up to and over stop projections arranged on the sleeve 400 as is shown in FIG. 26. The holder 300 is then prevented from moving axially relative to the sleeve 400 by virtue of engagement between the tapered circumferential projection TCP and the corresponding shaped recess in the surface ICS.

FIG. 30 shows another non-limiting embodiment of a blood collection device 100' according to the invention. The device 100' includes a generally cylindrical outer sleeve or outer body member 200' which includes a proximal end 200'*a* configured to allow an external needle N of a double-ended needle member or holder 300 to pass therethrough, and a distal end which can be closed off by a cap (not shown). An inner flange IF is arranged at the proximal end 200'*a*. The needle holder 300 has an outer circumferential surface OCS which frictionally engages with an inner circumferential surface ICS of a proximal end of an inner sleeve 400'. The surfaces ICS and OCS have generally corresponding shapes and need not be straight or cylindrical, i.e., they can also be, e.g., tapered or have an other non-straight shapes. The device 100' also includes a spring 600 which functions to move the needle holder 300 distally when the outer circumferential surface OCS of the needle holder 300 is released from frictional engagement with the inner circumferential surface ICS of the proximal end of the inner sleeve 400'. Once a user moves the cap 500 to the closed position, the sleeve 400' is caused to move axially in the proximal direction which, in turn, causes outer circumferential surface OCS of the needle holder 300 no longer frictionally engage with the inner circumferential surface ICS of the proximal end of the inner sleeve 400'. The spring 600 is then free to move the needle holder 300 within the sleeve 400' in a distal direction which ensures that the needle holder 300 is fully and safely arranged within the device 100. The device can then be safely handled and discarded.

The disengagement of the proximal end of the sleeve 400' from the needle holder 300 functions as follows. The sleeve 400' is prevented from moving axially backwards within the body 200' by a circumferential tapered shoulder (similar to shoulder TS' of FIG. 31), but is biased towards this direction by the spring 600 which, in FIG. 30, is almost fully compressed. The sleeve 400' has a plurality of proximal slots PS which divide the proximal end of the sleeve 400' into a plurality of spring fingers each having a portion of the surface ICS. A ring-shaped retaining sleeve RSS is movably mounted to the sleeve 400' and is movable between a locked position and the unlocked position shown in FIG. 30 which occurs upon movement of the ring RSS in the distal direction or more accurately movement of the sleeve 400' in the proximal direction while the sleeve RSS remains static, i.e., prevented from proximal movement by the shoulder ITS. When the sleeve 400' is moved in the proximal direction by the closing of the cap 500, the sleeve RSS contacts an annular surface the tapered shoulder ITS preventing the sleeve RSS from further movement in the proximal direction. The sleeve 400', however, continues to move in the proximal direction. When a point is reach where the sleeve RSS is moved sufficiently to the unlocked position (as is shown in FIG. 30), the spring fingers formed by the proximal slots PS are free to expand radially thereby releasing the engagement between the surface ICS of the sleeve 400' and the surface OCS of the holder 300. As a result, the proximal slots PS widen. This movement of the sleeve 400' and disengagement of the surfaces ICS and OCS is caused to occur automatically when the user moves the cap 500 to the closed position, and more specifically, when an annular surface or proximal end of cap 500 contacts an annular surface or distal end of the sleeve 400' and forces the sleeve 400' to move axially in the proximal direction.

Thus, when the user moves the cap 500 to the closed position (not shown), axial movement of the sleeve 400' and movement of the sleeve RSS relative to the sleeve 400' automatically causes the surface ICS to separate from the surface OCS. Since the frictional engagement between the surface ICS and the surface OCS constitutes the only engagement or connection between the holder 300 and the sleeve 400', the disengagement of these surfaces leaves the holder 300 free to move axially distally. Furthermore, because the spring 600 maintains a biasing force against the holder 300, when this engagement is released, the spring 600 will automatically expand axially and force the holder 300 to move distally within the sleeve 400'. This, in turn, results in the needle N being retracted into the sleeve 400' and positions it safely within the body 200'. The device 100' is then rendered unusable, i.e., cannot be reused, and can be safely handled and disposed of without fear of the needle causing injury to persons who handle the used device 100'.

As was the case with the previous embodiment, the sleeve 400', the retaining sleeve RSS, and the needle holder 300 constitute a sub-assembly. The proximal end of the sleeve 400' forms a plurality of arc-shaped sections or fingers divided by equally spaced slots PS. As such, these fingers are free to deflect outwardly or to slightly elastically deformed outwardly. However, the sleeve RSS functions to prevent this movement and ensures that the fingers are pressed tightly against the holder 300, and more specifically, that the surfaces OSC and ICS remain in engagement until the sleeve RSS is moved to a position which allows the fingers to deflect outwardly. In order to assemble this sub-assembly, one need only slide the holder 300 into the proximal end of the sleeve 400' and thereafter slide the sleeve RSS onto the distal end of the sleeve 400' and up to and over stop projections arranged on the sleeve 400'. The holder 300 is then prevented from moving axially relative to the sleeve 400' by virtue of engagement between the tapered circumferential projection TCP and the corresponding shaped recess or groove G in the surface ICS.

Figure 32:
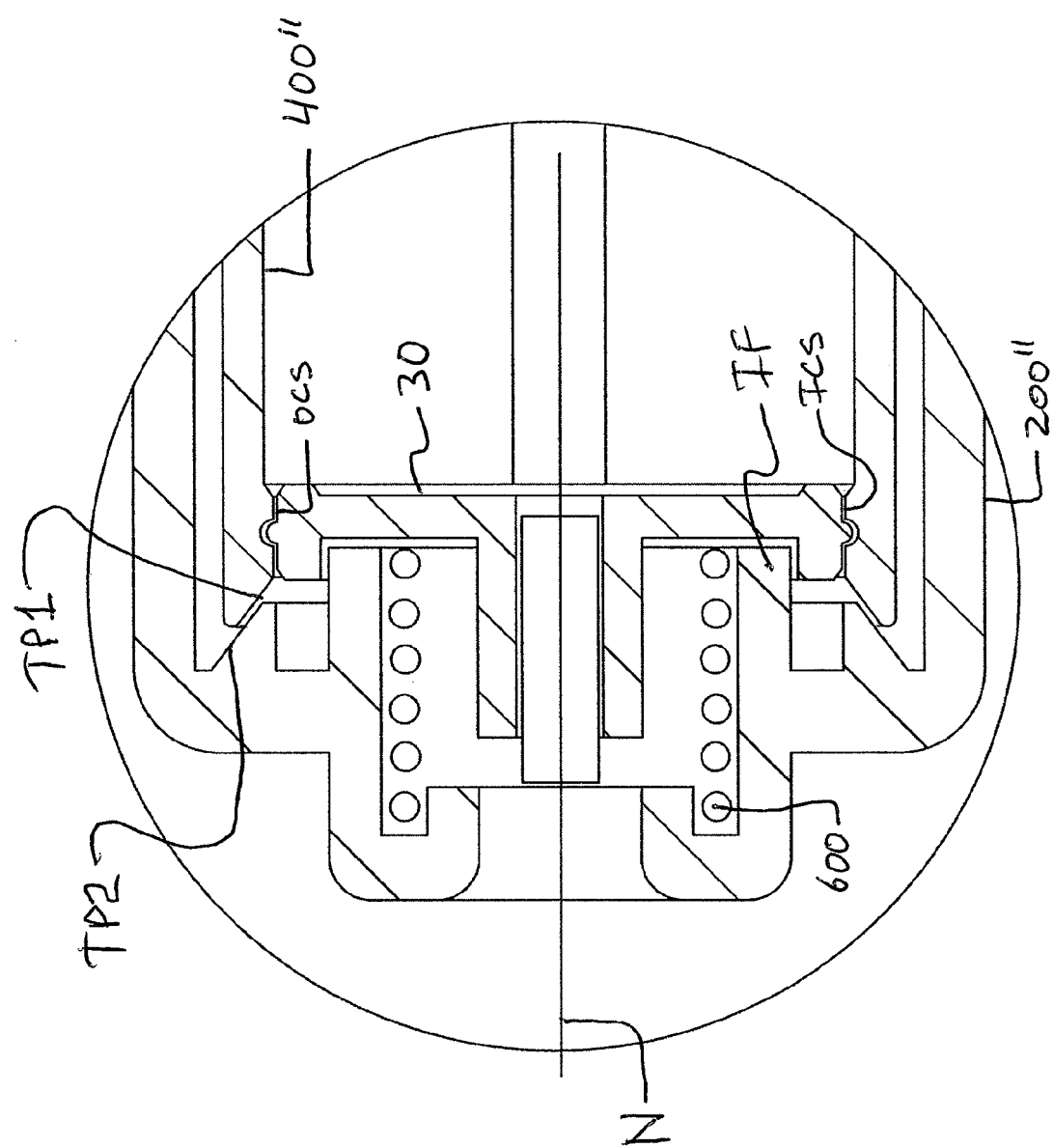
FIG. 32 shows an enlarged cross-section view of a portion of FIG. 31 and before the movable member is caused to release from engagement with the needle holding member.
Figure 33:
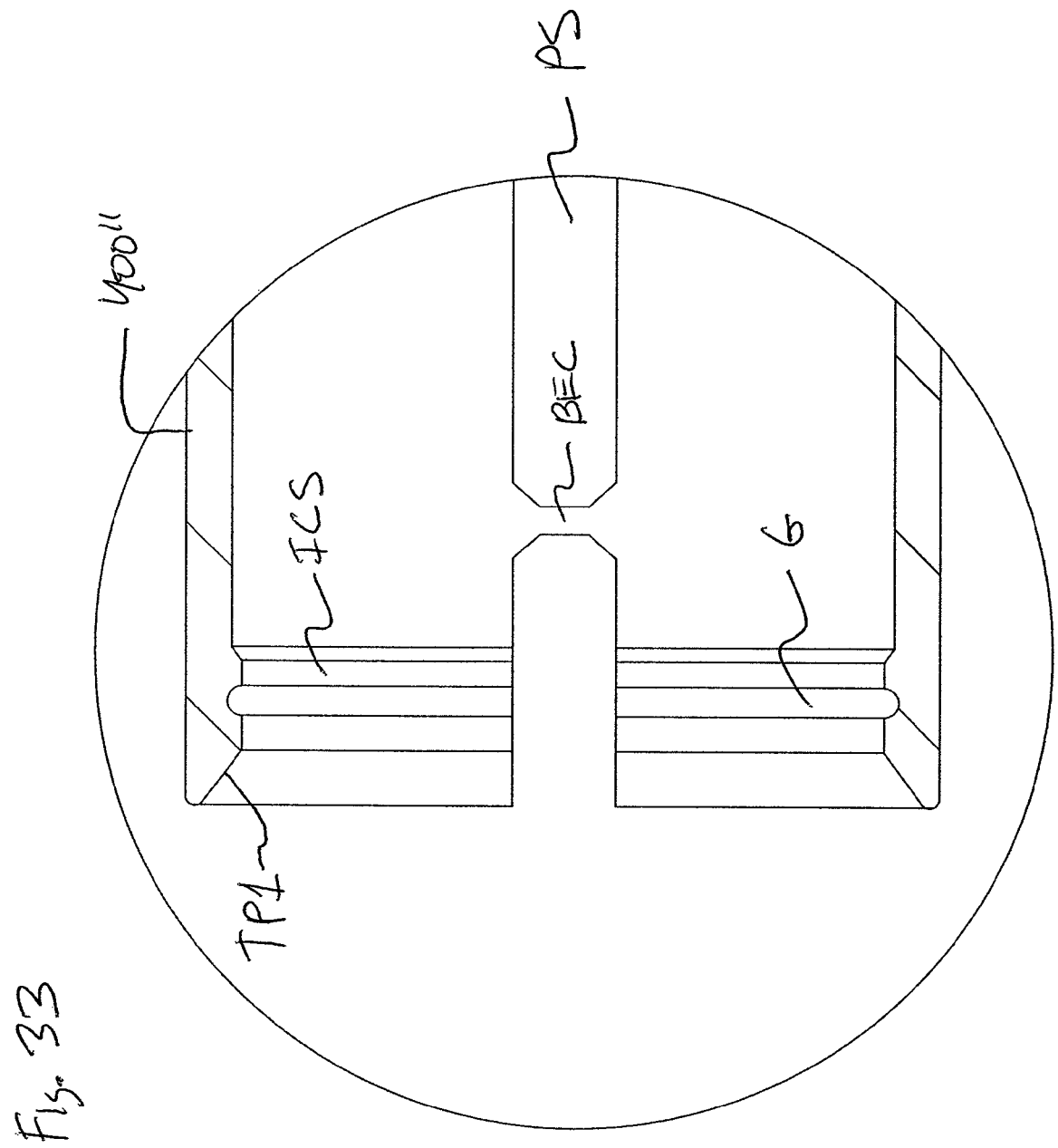
FIG. 33 shows an enlarged cross-section view of a proximal end of the sleeve used in the embodiment shown in FIG. 31.

FIGS. 31-33 show another non-limiting embodiment of a blood collection device 100" according to the invention. The device 100" includes a generally cylindrical outer sleeve or outer body member 200" which includes a proximal end 200"a configured to allow an external needle N of a double-ended needle member or holder 30 to pass therethrough, and a distal end which can be closed off by a cap 500'. An inner flange IF is arranged at the proximal end 200"a. The needle holder 30 has an outer circumferential surface OCS which frictionally engages with an inner circumferential surface ICS of a proximal end of an inner sleeve 400". The surfaces ICS and OCS have generally corresponding shapes and need not be straight or cylindrical, i.e., they can also be, e.g., tapered or have an other non-straight shapes. The device 100" also includes a spring 600 which functions to move the needle holder 30 distally when the outer circumferential surface OCS of the needle holder 30 is released from frictional engagement with the inner circumferential surface ICS of the proximal end of the inner sleeve 400". Once a user moves the cap 500' to the closed position, the sleeve 400" is caused to move axially in the proximal direction which, in turn, causes outer circumferential surface OCS of the needle holder 30 no longer frictionally engage with the inner circumferential surface ICS of the proximal end of the inner sleeve 400". The spring 600 is then free to move the needle holder 30 within the sleeve 400" in a distal direction which ensures that the needle holder 30 is fully and safely arranged within the device 100". The device can then be safely handled and discarded.

The disengagement of the proximal end of the sleeve 400" from the needle holder 30 functions as follows. The sleeve 400" is prevented from moving axially backwards within the body 200" by a circumferential tapered shoulder TS', but is biased towards this direction by the spring 600 which, in FIG. 31, is almost fully compressed. The sleeve 400" has a plurality of proximal slots PS which divide the proximal end of the sleeve 400" into a plurality of spring fingers each having a portion of the surface ICS. The proximal end of the spring fingers or the sleeve 400" includes a circumferential tapered portion TP1 which is configured to engage with an annular or circumferential tapered portion TP2 of the body 200" when the sleeve 400" is moved in the proximal direction by the cap 500'. Furthermore, when the sleeve 400" is moved in the proximal direction by the closing of the cap 500', the tapered surfaces TP1 of the spring fingers of the sleeve 400" contacts the tapered surface TP2 and causes the spring fingers formed by the proximal slots PS to expand radially thereby releasing the engagement between the surface ICS of the sleeve 400" and the surface OCS of the holder 30. As a result, the proximal slots PS widen. This movement of the sleeve 400" and disengagement of the surfaces ICS and OCS is caused to occur automatically when the user moves the cap 500' to the closed position, and more specifically, when an annular surface or proximal end of cap 500' contacts an annular surface or distal end of the sleeve 400" and forces the sleeve 400" to move axially in the proximal direction.

Thus, when the user moves the cap 500' to the closed position (not shown), axial movement of the sleeve 400" automatically causes the surface ICS to separate from the surface OCS. Since the frictional engagement between the surface ICS and the surface OCS constitutes the only engagement or connection between the holder 30 and the sleeve 400", the disengagement of these surfaces leaves the holder 30 free to move axially distally. Furthermore, because the spring 600 maintains a biasing force against the holder 30, when this engagement is released, the spring 600 will automatically expand axially and force the holder 30 to move distally within the sleeve 400". This, in turn, results in the needle N being retracted into the sleeve 400" and positions it safely within the body 200". The device 100" is then rendered unusable, i.e., cannot be reused, and can be safely handled and disposed of without fear of the needle causing injury to persons who handle the used device 100".

As was the case with some previous embodiments, the sleeve 400" and the needle holder 30 constitute a sub-assembly. The proximal end of the sleeve 400" forms a plurality of arc-shaped sections or fingers divided by equally spaced slots PS. The slots PS can be a few as two oppositely arranged slots or as many as, e.g., 20 or more, with any whole number between 2 and 20 being utilized. As such, these fingers are free to deflect outwardly or to slightly elastically deformed outwardly. However, the spring fingers include breakable and/or stretchable connections BEC (see FIG. 33) which are designed to break or stretch when the spring fingers are caused to radially expand beyond a certain point, as occurs when the surface TP1 engages with the surface TP2. These integrally formed members BEC also ensure that the fingers are pressed tightly against the holder 30, and more specifically, that the surfaces OSC and ICS remain in engagement until the surface TP1 engages significantly with the surface TP2 which allows the fingers to deflect outwardly. In order to assemble this sub-assembly, one need only slide the holder 30 into the proximal end of the sleeve 400". The holder 30 is then prevented from moving axially relative to the sleeve 400" by virtue of engagement between the projections CPP (see FIG. 16) and the corresponding shaped recess(es) or groove(s) in the surface ICS.

Figure 34:
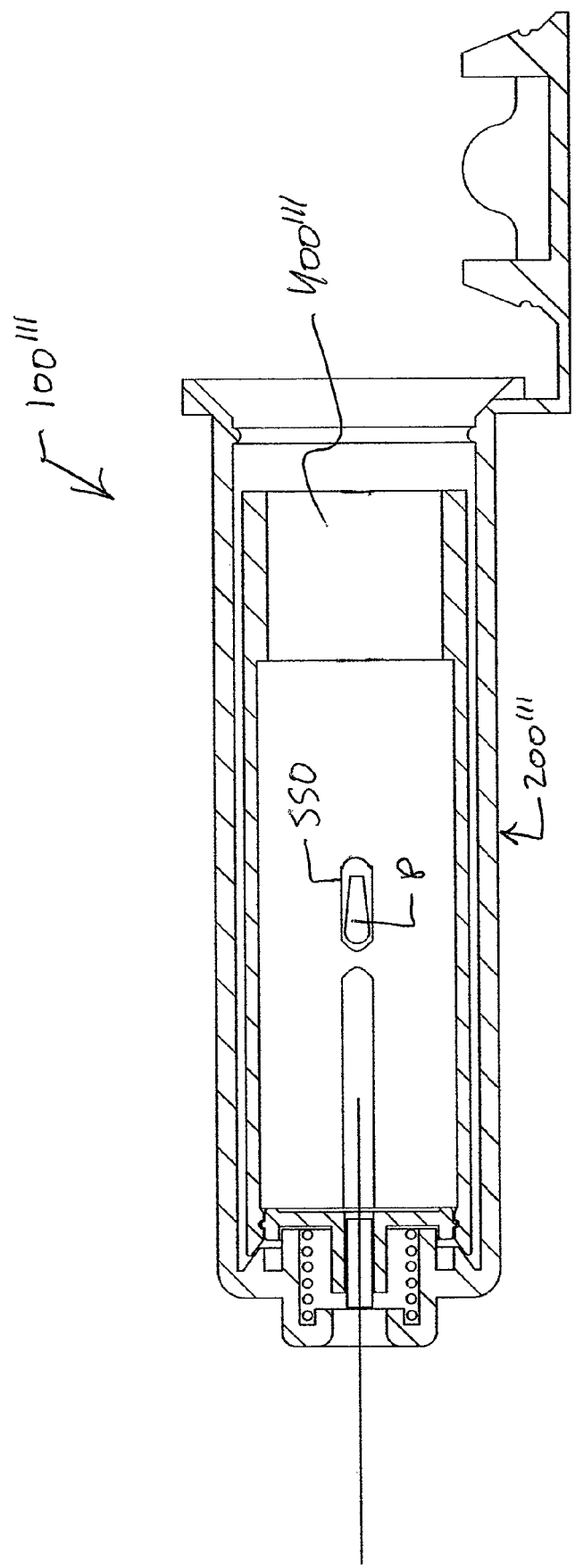
FIG. 34 shows a cross-section view of still another embodiment of the blood collection device. The device utilizes an annular outwardly tapered projection on an inside surface of the outer body which engages with an inwardly tapered leading end of the movable member to cause the front or proximal end of the movable member to expand radially when the movable member moves relative to the needle holding member. This would occur when the cap is moved to the closed position.

FIG. 34 show another non-limiting embodiment of a blood collection device 100''' according to the invention. The device 100''' includes all of the features of the embodiment of FIGS. 31-33, except that the sleeve 400''' a stop slot opening SSO which receives therein a projection P of the type used in the embodiment shown in FIG. 11, instead of the shoulder TS'. The device 100''' otherwise functions in the same way as that of FIGS. 31-33.

Figure 35:
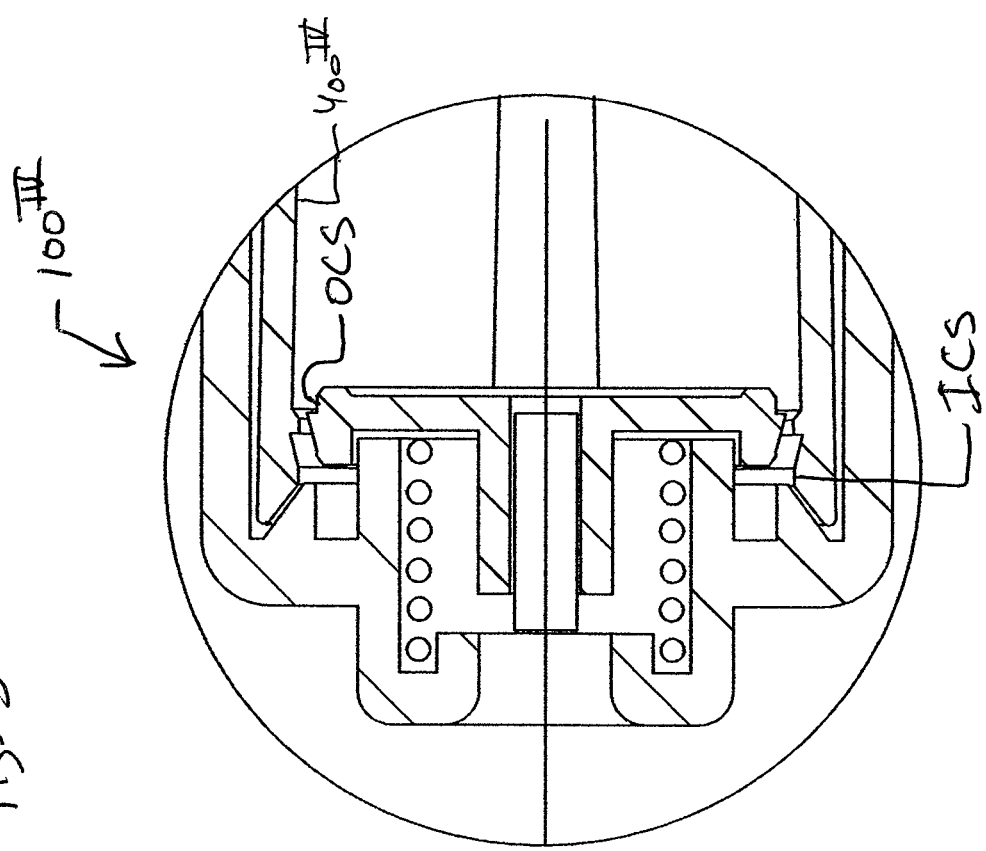
FIG. 35 shows an enlarged partial cross-section view of still another embodiment of the blood collection device. The device utilizes an annular outwardly tapered projection on an inside surface of the outer body which engages with an inwardly tapered leading end of the movable member to cause the front or proximal end of the movable member to expand radially when the movable member moves relative to the needle holding member. This would occur when the cap is moved to the closed position.
Figure 36:
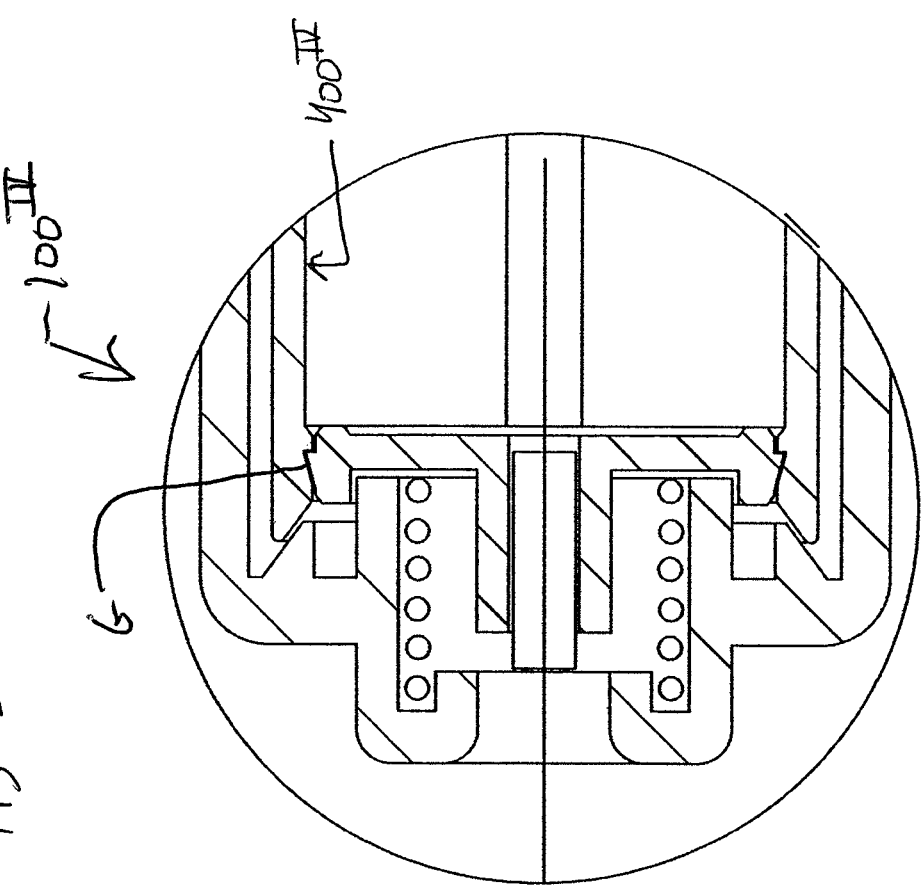
FIG. 36 shows the embodiment of FIG. 35 after the front or proximal end of the movable member is cause to expand radially when the movable member moves relative to the needle holding member and before the needle holding member moves to the retracted position. This would occur when the cap is moved to the closed position.

FIGS. 35-36 show another non-limiting embodiment of a blood collection device 100$^{IV}$ according to the invention. The device 100$^{IV}$ includes all of the features of the embodiment of FIGS. 31-33 or the embodiment of FIG. 34, except that the surface ICS utilizes a tapered groove G and the surface OCS utilizes either a continuous tapered circumferential projection which generally corresponds in shape to the groove G or a plurality of tapered projections having the configuration shown. The device 100$^{IV}$ otherwise functions in the same way as that of FIGS. 31-33.

Figure 38:
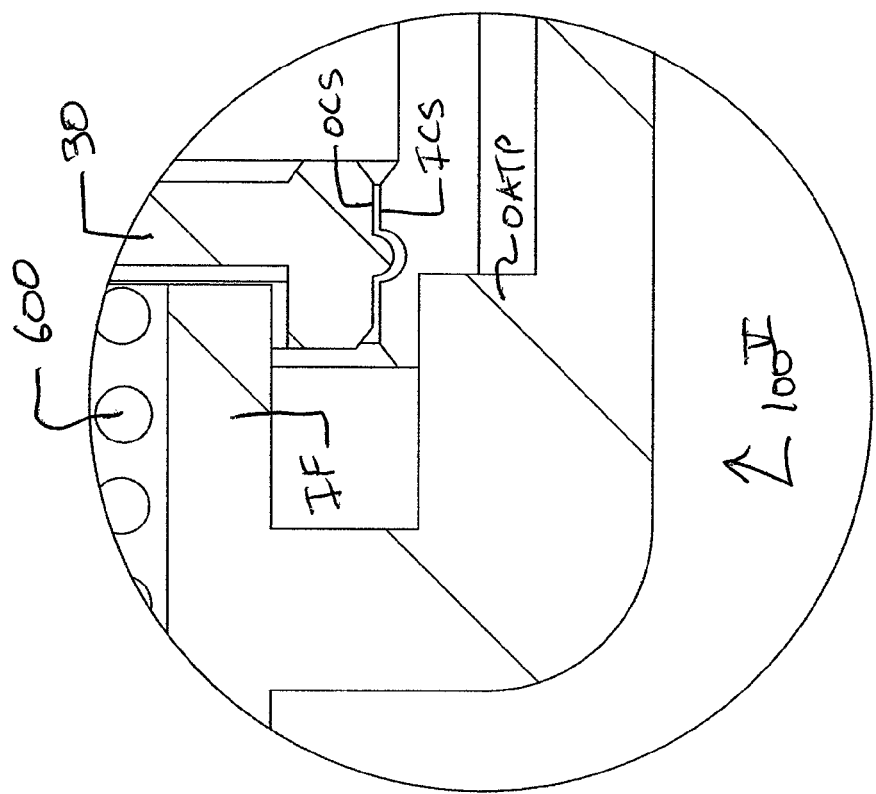
FIG. 38 shows an enlarged cross-section view of a portion of FIG. 37 rotated 90 degrees.
Figure 37:
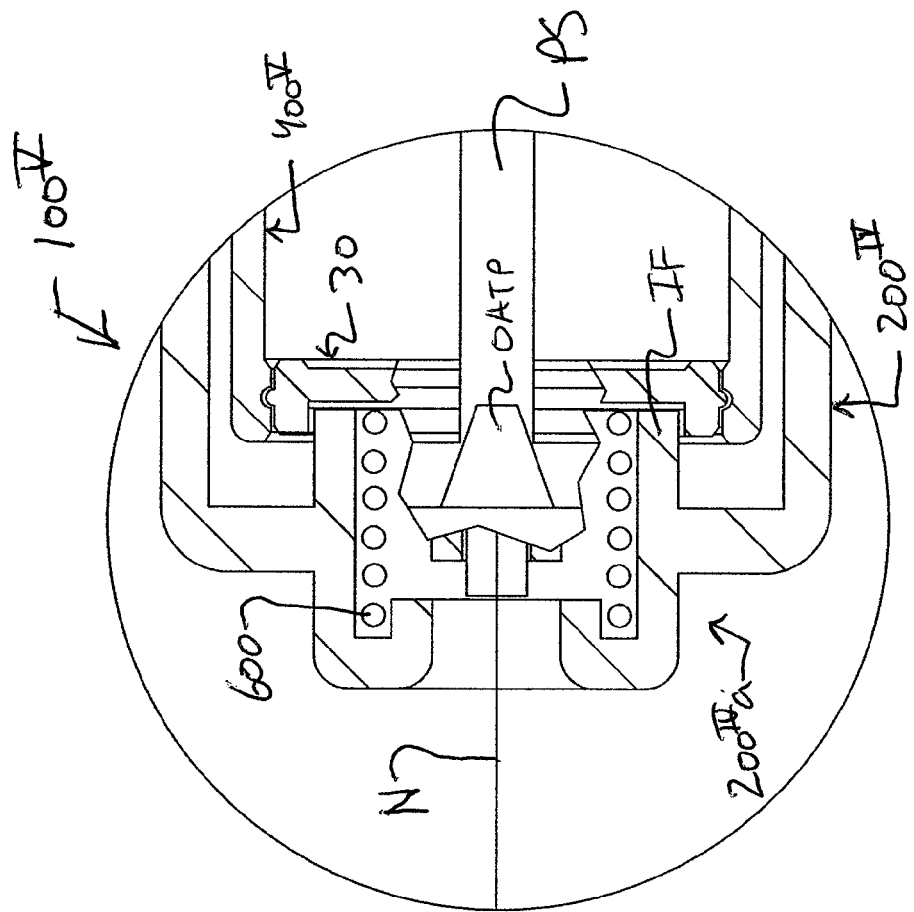
FIG. 37 shows an enlarged partial cross-section view of still another embodiment of the blood collection device. The device utilizes one or more tapered projections on an inside surface of the outer body which engages with one or more slots in the leading end of the movable member to cause the front or proximal end of the movable member to expand radially when the movable member moves relative to the needle holding member. This would occur when the cap is moved to the closed position.

FIGS. 37 and 38 show another non-limiting embodiment of a blood collection device 100$^V$ according to the invention. The device 100$^V$ includes a generally cylindrical outer sleeve or outer body member 200$^{IV}$ which includes a proximal end 200$^V$a configured to allow an external needle N of a double-ended needle member or holder 30 to pass therethrough, and a distal end which can be closed off by a cap (not shown). An inner flange IF is arranged at the proximal end 200$^{IV}$a. The needle holder 30 has an outer circumferential surface OCS which frictionally engages with an inner circumferential surface ICS of a proximal end of an inner sleeve 400$^{IV}$. The sleeve 400$^V$ can have a configuration similar to that of FIG. 18 except that the taper TDE is not utilized, and instead the distal end is configured to be similar to the distal end shown in the sleeve 400" of FIG. 31. The surfaces ICS and OCS have generally corresponding shapes and need not be straight or cylindrical, i.e., they can also be, e.g., tapered or have another non-straight shapes. The device 100$^V$ also includes a spring 600 which functions to move the needle holder 30 distally when the outer circumferential surface OCS of the needle holder 30 is released from frictional engagement with the inner circumferential surface ICS of the proximal end of the inner sleeve 400$^V$. Once a user moves the cap to the closed position, the sleeve 400$^V$ is caused to move axially in the proximal direction which, in turn, causes outer circumferential surface OCS of the needle holder 30 no longer frictionally engage with the inner circumferential surface ICS of the proximal end of the inner sleeve 400$^V$. The spring 600 is then free to move the needle holder 30 within the sleeve 400$^V$ in a distal direction which ensures that the needle holder 30 is fully and safely arranged within the device 100$^V$. The device can then be safely handled and discarded.

The disengagement of the proximal end of the sleeve 400$^V$ from the needle holder 30 functions as follows. The sleeve 400$^V$ is prevented from moving axially backwards within the body 200$^{IV}$ by either a circumferential tapered shoulder (similar to shoulder TS' of FIG. 31) or by projections (similar to projections P of FIG. 11), and is biased towards this distal direction by the spring 600 which, in FIG. 37, is almost fully compressed. The sleeve 400$^V$ has a plurality of proximal slots PS which divide the proximal end of the sleeve 400$^V$ into a plurality of spring fingers each having a portion of the surface ICS. The body 200$^{IV}$ includes two oppositely arranged tapered projections OATP arranged therein which are each configured to engage (i.e., wedge open) with one of the proximal slots PS of the sleeve 400$^V$ when the sleeve 400$^V$ is moved in the proximal direction by the cap. Furthermore, when the sleeve 400$^V$ is moved in the proximal direction by the closing of the cap, the tapered surfaces of the projections OATP are contacted the side surfaces of the spring fingers defined by the slots PS and causes the spring fingers formed by the proximal slots PS to expand radially thereby releasing the engagement between the surface ICS of the sleeve 400$^V$ and the surface OCS of the holder 30. As a result, the proximal slots PS widen. This movement of the sleeve 400$^V$ and disengagement of the surfaces ICS and OCS is caused to occur automatically when the user moves the cap to the closed position, and more specifically, when an annular surface or proximal end of cap contacts an annular surface or distal end of the sleeve 400$^V$ and forces the sleeve 400$^V$ to move axially in the proximal direction.

Thus, when the user moves the cap to the closed position (not shown), axial movement of the sleeve 400$^V$ automatically causes the surface ICS to separate from the surface OCS. Since the frictional engagement between the surface ICS and the surface OCS constitutes the only engagement or connection between the holder 30 and the sleeve 400$^V$, the disengagement of these surfaces leaves the holder 30 free to move axially distally. Furthermore, because the spring 600 maintains a biasing force against the holder 30, when this engagement is released, the spring 600 will automatically expand axially and force the holder 30 to move distally within the sleeve 400$^V$. This, in turn, results in the needle N being retracted into the sleeve 400$^V$ (similar to the way shown in FIG. 39) and positions it safely within the body 200$^{IV}$. The device 100$^V$ is then rendered unusable, i.e., cannot be reused, and can be safely handled and disposed of without fear of the needle causing injury to persons who handle the used device 100$^V$.

As was the case with some previous embodiments, the sleeve 400$^V$ and the needle holder 30 constitute a sub-assembly. The proximal end of the sleeve 400$^V$ forms a plurality of arc-shaped sections or fingers divided by equally spaced slots PS. The slots PS can be a few as two oppositely arranged slots or as many as, e.g., 20 or more, with any whole number between 2 and 20 being utilized. As such, these fingers are free to deflect outwardly or to slightly elastically deformed outwardly. Furthermore, the spring fingers can include breakable and/or stretchable connections (similar to connections BEC shown in FIG. 33) which are designed to break or stretch when the spring fingers are caused to radially expand beyond a certain point, as occurs when the slots PS engages with the tapered surfaces of the projections OATP. These integrally formed members BEC also ensure that the fingers are pressed tightly against the holder 30, and more specifically, that the surfaces OSC and ICS remain in engagement until the slots PS engage with the tapered surfaces of the projections OATP which allows the fingers to deflect outwardly. In order to assemble this sub-assembly, one need only slide the holder 30 into the proximal end of the sleeve 400$^V$. The holder 30 is then prevented from moving axially relative to the sleeve 400$^V$ by virtue of engagement between the projections CPP (see FIG. 16) and the corresponding shaped recess(es) or groove(s) in the surface ICS.

Figure 39:
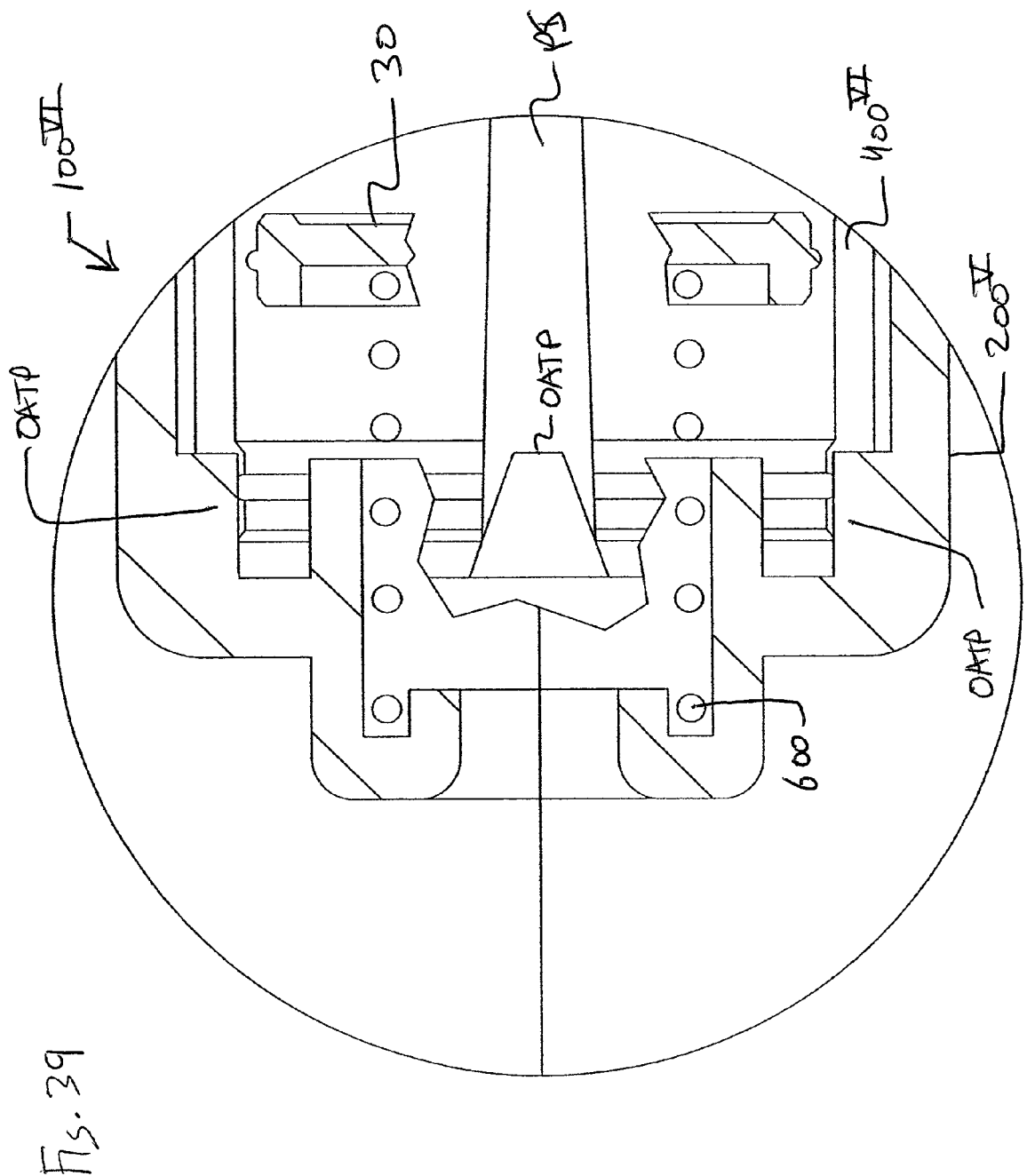
FIG. 39 shows an enlarged cross-section view of another embodiment. This embodiment is similar to that of FIG. 37 except that it utilizes four proximal slots and four proximal slot expanding projections arranged in the body. The figure shows the device after the movable member or sleeve is caused to release from engagement with the needle holding member.

FIG. 39 shows another non-limiting embodiment of a blood collection device 100$^{VI}$ according to the invention. The device 100$^{VI}$ includes all of the features of the embodiment of FIGS. 27-38, except that instead of two proximal slots PS, the sleeve 400$^{VI}$ utilizes four proximal slots PS, and the body 200$^V$ utilizes four equally angularly spaced projections OATP instead of just two oppositely arranged projections. The device 100$^{VI}$ otherwise functions in the same way as that of FIGS. 37-38.

Figure 40:
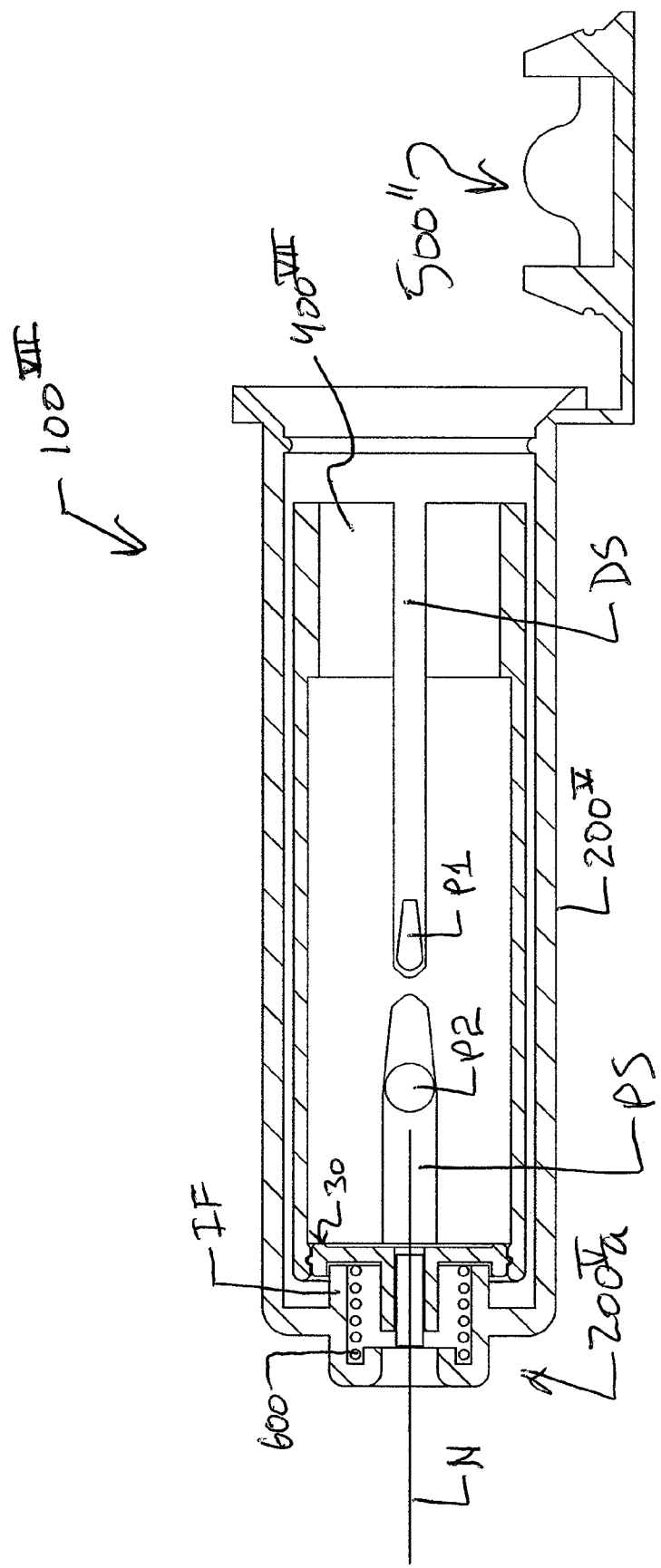
FIG. 40 shows a side cross-section view of still another embodiment of the blood collection device. The device utilizes one or more circular projections on an inside surface of the outer body which engages with one or more tapered slots in the movable member to cause the front or proximal end of the movable member to expand radially when the movable member moves relative to the needle holding member. This would occur when the cap is moved to the closed position.
Figure 41:
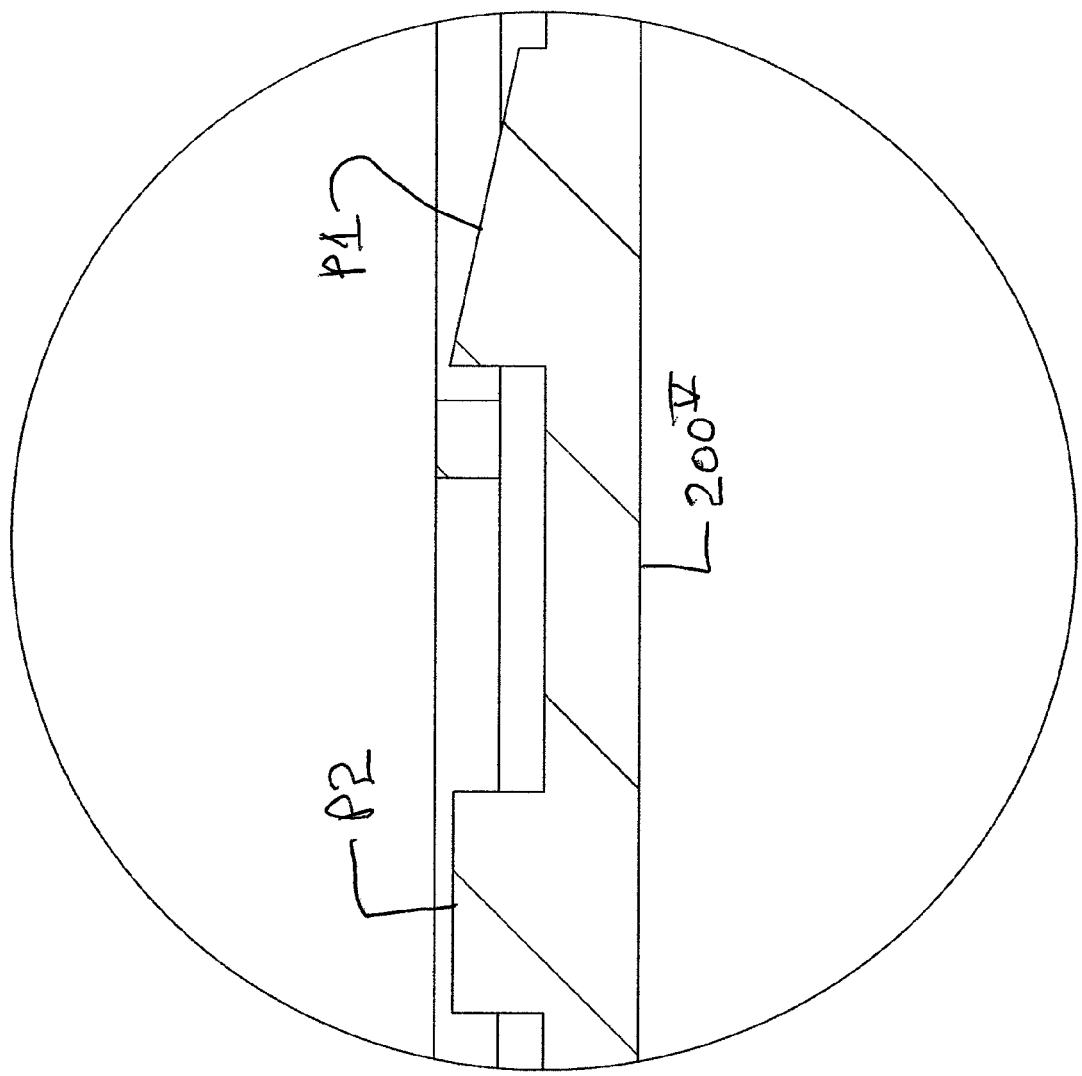
FIG. 41 shows an enlarged top cross-section view of a portion of the tubular outer body and the movable member used in the embodiment shown in FIG. 40.

FIGS. 40 and 41 show another non-limiting embodiment of a blood collection device 100$^{VII}$ according to the invention. The device 100$^{VII}$ includes a generally cylindrical outer sleeve or outer body member 200$^V$ which includes a proximal end 200$^V a$ configured to allow an external needle N of a double-ended needle member or holder 30 to pass therethrough, and a distal end which can be closed off by a cap 500". An inner flange IF is arranged at the proximal end 200$^V a$. The needle holder 30 has an outer circumferential surface OCS which frictionally engages with an inner circumferential surface ICS of a proximal end of an inner sleeve 400$^{VII}$. The sleeve 400$^{VII}$ can have a configuration similar to that of FIG. 18 except that the taper TDE is not utilized, and the proximal slots PS are made wider than the distal slots DS. The surfaces ICS and OCS have generally corresponding shapes and need not be straight or cylindrical, i.e., they can also be, e.g., tapered or have an other non-straight shapes. The device 100$^{VII}$ also includes a spring 600 which functions to move the needle holder 30 distally when the outer circumferential surface OCS of the needle holder 30 is released from frictional engagement with the inner circumferential surface ICS of the proximal end of the inner sleeve 400$^{VII}$. Once a user moves the cap 500" to the closed position, the sleeve 400$^{VII}$ is caused to move axially in the proximal direction which, in turn, causes outer circumferential surface OCS of the needle holder 30 no longer frictionally engage with the inner circumferential surface ICS of the proximal end of the inner sleeve 400$^{VII}$. The spring 600 is then free to move the needle holder 30 within the sleeve 400$^{VII}$ in a distal direction which ensures that the needle holder 30 is fully and safely arranged within the device 100$^{VII}$. The device can then be safely handled and discarded.

The disengagement of the proximal end of the sleeve 400$^{VII}$ from the needle holder 30 functions as follows. The sleeve 400$^{VII}$ is prevented from moving axially backwards within the body 200$^V$ by the oppositely arranged projections P1, and is biased towards this distal direction by the spring 600 which, in FIG. 40, is almost fully compressed. The sleeve 400$^{VII}$ has a plurality of proximal slots PS which divide the proximal end of the sleeve 400$^{VII}$ into a plurality of spring fingers each having a portion of the surface ICS. The body 200$^V$ includes two oppositely arranged circular projections P2 arranged therein which are each configured to engage (i.e., wedge open) with one of the proximal slots PS of the sleeve 400$^{VII}$ when the sleeve 400$^{VII}$ is moved in the proximal direction by the cap 500". Furthermore, when the sleeve 400$^{VII}$ is moved in the proximal direction by the closing of the cap 500", the tapered surfaces of the proximal slot PS are contacted the circular surface of the projection P2 and this causes the spring fingers formed by the proximal slots PS to expand radially thereby releasing the engagement between the surface ICS of the sleeve 400$^{VII}$ and the surface OCS of the holder 30. As a result, the proximal slots PS widen. This movement of the sleeve 400$^{VII}$ and disengagement of the surfaces ICS and OCS is caused to occur automatically when the user moves the cap 500" to the closed position, and more specifically, when an annular surface or proximal end of cap 500" contacts an annular surface or distal end of the sleeve 400$^{VII}$ and forces the sleeve 400$^{VII}$ to move axially in the proximal direction.

Thus, when the user moves the cap 500" to the closed position (not shown), axial movement of the sleeve 400$^{VII}$ automatically causes the surface ICS to separate from the surface OCS. Since the frictional engagement between the surface ICS and the surface OCS constitutes the only engagement or connection between the holder 30 and the sleeve 400$^{VII}$, the disengagement of these surfaces leaves the holder 30 free to move axially distally. Furthermore, because the spring 600 maintains a biasing force against the holder 30, when this engagement is released, the spring 600 will automatically expand axially and force the holder 30 to move distally within the sleeve 400$^{VII}$. This, in turn, results in the needle N being retracted into the sleeve 400$^{VII}$ and positions it safely within the body 200$^V$. The device 100$^{VII}$ is then rendered unusable, i.e., cannot be reused, and can be safely handled and disposed of without fear of the needle causing injury to persons who handle the used device 100$^{VII}$.

As was the case with some previous embodiments, the sleeve 400$^{VII}$ and the needle holder 30 constitute a sub-assembly. The proximal end of the sleeve 400$^{VII}$ forms a plurality of arc-shaped sections or fingers divided by equally spaced slots PS. The slots PS can be a few as two oppositely arranged slots or as many as, e.g., 20 or more, with any whole number between 2 and 20 being utilized. As such, these fingers are free to deflect outwardly or to slightly elastically deformed outwardly. Furthermore, the spring fingers can include breakable and/or stretchable connections (similar to connections BEC shown in FIG. 33) which are designed to break or stretch when the spring fingers are caused to radially expand beyond a certain point, as occurs when the slots PS engages with the circular projections P2. These integrally formed members BEC also ensure that the fingers are pressed tightly against the holder 30, and more specifically, that the surfaces OSC and ICS remain in engagement until the tapered surfaces of the slots PS engage with the circular projections P2 which allows the fingers to deflect outwardly. In order to assemble this sub-assembly, one need only slide the holder 30 into the proximal end of the sleeve 400$^{VII}$. The holder 30 is then prevented from moving axially relative to the sleeve 400$^{VII}$ by virtue of engagement between the projections CPP (see FIG. 16) and the corresponding shaped recess(es) or groove(s) in the surface ICS.

Figure 42:
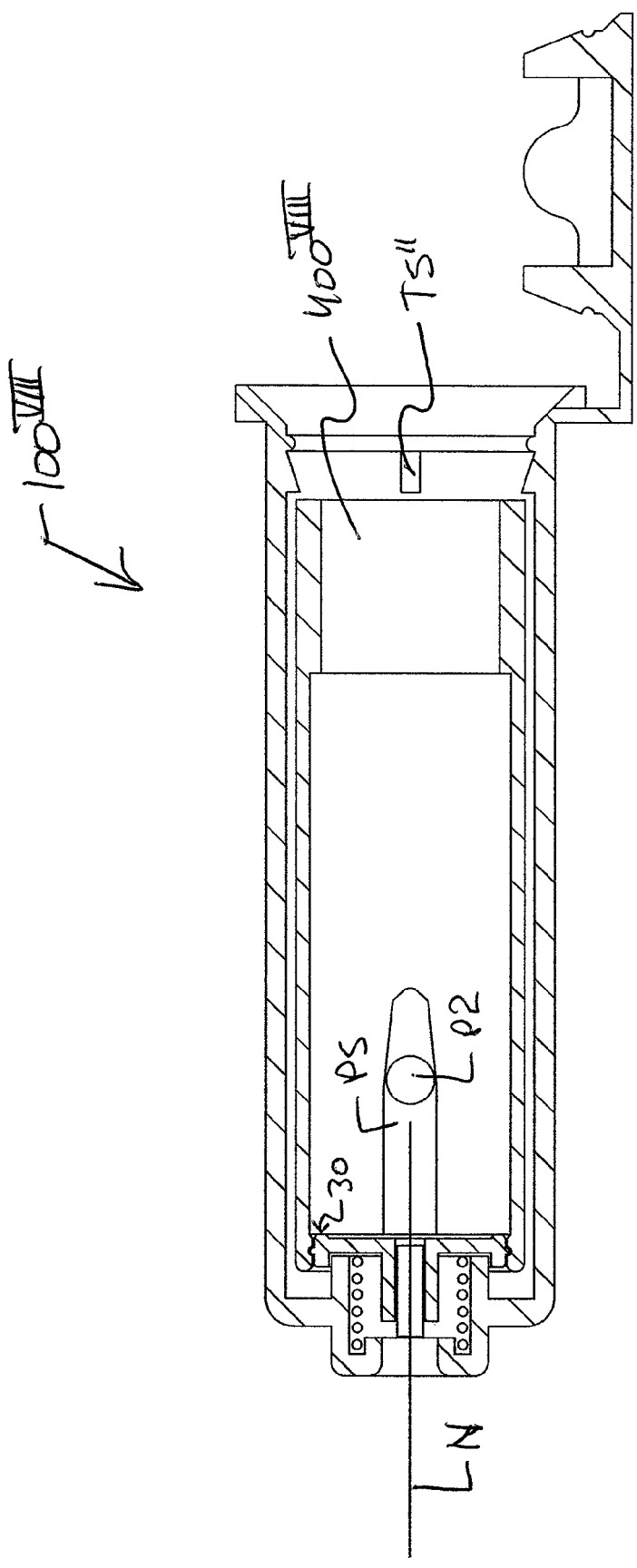
FIG. 42 shows a side cross-section view of still another embodiment of the blood collection device. The device utilizes one or more circular projections on an inside surface of the outer body which engages with one or more tapered slots in the movable member to cause the front or proximal end of the movable member to expand radially when the movable member moves relative to the needle holding member. This would occur when the cap is moved to the closed position.

FIG. 42 shows another non-limiting embodiment of a blood collection device 100$^{VIII}$ according to the invention. The device 100$^{VIII}$ includes all of the features of the embodiment of FIGS. 40-41, except that the projections P1 and the distal slots DS are not utilized, and instead tapered stop shoulder projections TS" are utilized to prevent distal movement of the sleeve 400$^{VIII}$. The device 100$^{VIII}$ otherwise functions in the same way as that of FIGS. 40-41.

The devices described above can also utilize one or more features disclosed in the prior art documents expressly incorporated by reference herein. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A retractable medical device comprising:
   a body having and a back end that is at least one of open and sized and configured to receive therein a receptacle;
   a movable member arranged within the body, the movable member having a back end and a front end;
   a needle holding member arranged in an area of the front end of the movable member; and
   a spring structured and arranged to move the needle holding member to a retracted position within the movable member when the movable member experiences at least one of:
     the front end of the movable member is caused to expand generally radially;
     the back end of the movable member is caused to contract generally radially;
     the front end of the movable member is caused to expand generally radially when the back end of the movable member is caused to contract generally radially;
     axial movement caused by a cap closing off the back end of the body, wherein, during the closing off of the back end of the body, a tapered surface of the back end of the movable member is contacted by a portion of the cap;
     circumferential portions of the front end of the movable member are caused to expand outwardly or generally radially so as to allow the needle holding member to disengage from the front end of the movable member; and
     portions of the front end of the movable member separated by slots are caused to expand outwardly or generally radially so as to allow the needle holding member to disengage from the front end of the movable member.

2. The device of claim 1, wherein the body and the movable members are at least one of generally cylindrical and generally tubular.

3. The device of claim 1, wherein the movable member is sized and configured to at least partially receive therein the receptacle and the receptacle is one of a fluid collection tube and an evacuated blood collection receptacle.

4. The device of claim 1, wherein an outer peripheral surface of the needle holding member frictionally engages with an inner surface of the front end of the movable member.

5. The device of claim 1, wherein an outer peripheral surface of the needle holding member comprises at least one projection which engages with at least one recess arranged on an inner surface of the front end of the movable member.

6. The device of claim 1, wherein an outer peripheral surface of the needle holding member comprises at least one recess which engages with at least one projection arranged on an inner surface of the front end of the movable member.

7. The device of claim 1, wherein the body comprises a device arranged within the body for limiting axial movement of the movable member within the body.

8. The device of claim 1, further comprising a cap structure and arranged to close off a back end of the body.

9. The device of claim 1, further comprising a cap connected by a living hinge to the body.

10. The device of claim 1, further comprising a cap having a portion which contacts the back end of the movable member.

11. The device of claim 1, further comprising a cap having tapered surfaces which contact tapered surfaces of the back end of the movable member.

12. The device of claim 1, further comprising a cap structured and arranged to lock to the back end of the body.

13. The device of claim 1, further comprising a cap structured and arranged to cause the needle holding member to move to the retracted position by the spring when the cap is locked to the body.

14. The device of claim 1, further comprising a cap structured and arranged to cause the needle holding member to move to the retracted position by the spring when the cap closes off the back end of the body.

15. The device of claim 1, further comprising a cap structured and arranged to cause the needle holding member to move to the retracted position by the spring when the cap engages with a back end of the movable member.

16. The device of claim 1, wherein the movable member comprises an internal surface which limits retraction movement of the needle holding member.

17. The device of claim 1, wherein the movable member comprises an internal annular surface which limits retraction movement of the needle holding member.

18. The device of claim 1, wherein the needle holding member is structured and arranged to support a double-ended needle.

19. The device of claim 1, wherein the needle holding member is structured and arranged to retain a removable double-ended needle.

20. The device of claim 1, further comprising a cap having an outer rim larger than an opening in the back of the body and an inner rim comprising at least one protrusion structured and arranged to engage with the back end of the movable member.

21. The device of claim 1, further comprising a cap having an outer rim larger than an opening in the back of the body and at least two oppositely arranged protrusions structured and arranged to engage with the back end of the movable member.

22. The device of claim 1, further comprising a cap having an outer rim larger than an opening in the back of the body and at least two oppositely arranged tapered protrusions structured and arranged to engage with tapered surfaces of the back end of the movable member.

23. The device of claim 1, wherein the movable member comprises oppositely arranged elongated slots extending to the front end of the movable member, whereby a width of the elongated slots changes when the needle holding member is caused to move to the retracted position.

24. The device of claim 1, wherein the movable member comprises oppositely arranged elongated slots extending to the back end of the movable member, whereby a width of the elongated slots changes when the needle holding member is caused to move to the retracted position.

25. The device of claim 1, wherein the movable member comprises oppositely arranged first elongated slots extending to the front end of the movable member and oppositely arranged second elongated slots extending to the back end of the movable member, whereby a width of the elongated first and second slots changes when the needle holding member is caused to move to the retracted position.

26. The device of claim 1, wherein the movable member comprises first elongated slots extending to the front end of the movable member and second elongated slots extending to the back end of the movable member, whereby a width of the elongated first and second slots changes when the needle holding member is caused to move to the retracted position.

27. The device of claim 1, wherein the movable member comprises first elongated slots extending to the front end of the movable member, second elongated slots extending to the back end of the movable member, and a connecting portion disposed between the first and second elongated slots, whereby a width of the elongated first and second slots changes when the needle holding member is caused to move to the retracted position.

28. The device of claim 1, wherein the movable member comprises two-semi-cylindrical members which, when arranged to form a cylindrical member, form first elongated slots extending to the front end of the movable member, second elongated slots extending to the back end of the movable member, and a connecting portion disposed between the first and second elongated slots, whereby a width of the elongated first and second slots changes when the needle holding member is caused to move to the retracted position.

29. The device of claim 1, wherein the movable member comprises at least one elongated slot extending to the front end of the movable member and a tapered surface arranged at the front end of the movable member which is structured and arranged to engage a tapered surface inside the body to thereby cause the needle holding member to move to the retracted position.

30. The device of claim 1, wherein the movable member comprises at least two oppositely arranged slots extending to the front end of the movable member and a tapered surface arranged at the front end of the movable member which is structured and arranged to engage a tapered surface inside the body to thereby cause the needle holding member to move to the retracted position.

31. The device of claim 1, wherein the movable member comprises at least one slot extending to the front end of the movable member and the body comprises at least one projection having tapered surfaces which are structured and arranged to engage the at least one slot to thereby cause the needle holding member to move to the retracted position.

32. The device of claim 1, wherein the movable member comprises at least one slot arranged on the front end of the movable member and the body comprises at least one projection having tapered surfaces, and wherein the slot engages with the tapered surfaces, a width of the at least one slot changes to thereby cause the needle holding member to move to the retracted position.

33. The device of claim 1, wherein the movable member comprises at least two oppositely arranged slots arranged on the front end of the movable member and the body comprises at least two oppositely arranged projections each having tapered surfaces, and wherein each slot engages with each set of the tapered surfaces, a width of each slot changes to thereby cause radial expansion of the front end of the movable member.

34. The device of claim 1, wherein the movable member comprises at least one slot extending to the front end of the movable member and the body comprises at least one projection arranged in an inner cylindrical surface of the body between the front end and the back end of the body, and wherein the at least one slot comprises tapered surfaces structured and arranged to engage with the at least one projection, whereby a width of the at least one slot changes when the movable member moves axially within the body and when the tapered surfaces engage with the at least one projection.

35. The device of claim 1, wherein the body comprises at least one projection arranged in an inner cylindrical surface of the body between the front end and the back end of the body and wherein the at least one projection is structured and arranged to serve as an axle which allows portions of the movable member to pivot about the axle.

36. The device of claim 1, wherein the body comprises oppositely arranged projections arranged in an inner cylindrical surface of the body between the front end and the back end of the body and wherein each projection is structured and arranged to serve as an axle which allows portions of the movable member to pivot about the axle.

37. A retractable medical device comprising:
a tubular body having a front end and a back end that is sized and configured to receive therein a fluid collection tube or an evacuated blood collection receptacle;
a movable sleeve arranged within the body, the movable sleeve having a back end and a front end;
the movable sleeve being sized and configured to at least partially receive therein one of the fluid collection tube and the evacuated blood collection receptacle;
a needle holding member comprising a centrally disposed opening for receiving a double-ended needle and being axially retained in an area of the front end of the movable sleeve;
a spring structured and arranged to move the needle holding member to a retracted position within the movable sleeve; and
a cap structured and arranged to close-off the back end of the tubular body,
wherein, when the cap is positioned to close-off the back end of the tubular body, at least one of:
the movable sleeve experiences axial movement which participates in causing the front end of the movable sleeve to expand generally radially so as to allow the needle holding member to disengage from the front end of the movable sleeve and move to the retracted position;
the back end of the movable sleeve experiences radial contraction which causes the front end of the movable sleeve to expand generally radially so as to allow the needle holding member to disengage from the front end of the movable sleeve and move to the retracted position;
the back end of the movable sleeve experiences radial contraction which causes portions of the front end of the movable sleeve to pivot open so as to allow the needle holding member to disengage from the front end of the movable sleeve and move to the retracted position;
spaced apart portions of the front end of the movable sleeve are caused to expand outwardly so as to allow the needle holding member to disengage from the front end of the movable sleeve;

circumferential portions of the front end of the movable sleeve are caused to expand outwardly so as to allow the needle holding member to disengage from the front end of the movable sleeve; and portions of the front end of the movable sleeve separated by slots are caused to expand outwardly so as to allow the needle holding member to disengage from the front end of the movable sleeve.

38. A single-use blood sampling device comprising:

a tubular body having an open back end and a front end;

a sleeve arranged within the body, the sleeve having a back end and a front end;

the sleeve being sized and configured to at least partially receive therein one of a fluid collection tube and an evacuated blood collection receptacle;

a needle holding member comprising a centrally disposed opening for receiving a double-ended needle and being axially retained in an area of the front end of the sleeve;

a spring structured and arranged to move the needle holding member to a retracted position within the sleeve; and a cap structured and arranged to close-off the back end of the tubular body, wherein, when the cap is positioned to close-off the back end of the body, the needle holding member is automatically caused to move to the retracted position within the sleeve as a result of at least one of:

the sleeve experiencing axial movement which participates in causing the front end of the sleeve to expand generally radially;

the back end of the sleeve experiencing radial contraction which causes the front end of the sleeve to expand generally radially;

the back end of the sleeve experiencing radial contraction which causes portions of the front end of the sleeve to pivot open;

spaced apart portions of the front end of the sleeve are caused to expand outwardly so as to allow the needle holding member to disengage from the front end of the sleeve;

circumferential portions of the front end of the sleeve are caused to expand outwardly so as to allow the needle holding member to disengage from the front end of the sleeve; and portions of the front end of the sleeve separated by slots are caused to expand outwardly so as to allow the needle holding member to disengage from the front end of the sleeve.

39. A method of taking a fluid sample using the device of claim 1, the method comprising:

inserting a receptacle into the device;

removing the receptacle from the device; and placing a cap onto the back end of the body to thereby cause the needle holding member to move to the retracted position.

40. A method of taking a fluid sample using the device of claim 1, the method comprising:

inserting a receptacle into the device;

removing the receptacle from the device; and placing the cap onto the back end of the tubular body to thereby cause the needle holding member to move to the retracted position.

41. A method of taking a fluid sample using the device of claim 1, the method comprising:

inserting a receptacle into the device;

removing the receptacle from the device; and placing the cap onto the back end of the tubular body to thereby cause the needle holding member to move to the retracted position.

42. The device of claim 1, further comprising a releasable connection mechanism structured and arranged to releasably connect the needle holding member to the movable member.

43. The device of claim 42, wherein the releasable connection mechanism comprises at least one projection and at least one recess.

44. The device of claim 1, wherein the needle holding member is frictionally disengagable from the movable member when the front end of the movable member expands generally radially.

* * * * *